United States Patent
Wienert

(10) Patent No.: US 12,237,070 B2
(45) Date of Patent: Feb. 25, 2025

(54) METHOD OF DETERMINING AND DISPLAYING AN AREA OF INTEREST OF A DIGITAL MICROSCOPE TISSUE IMAGE, INPUT/OUTPUT SYSTEM FOR NAVIGATING A PATIENT-SPECIFIC IMAGE RECORD, AND WORK PLACE COMPRISING SUCH INPUT/OUTPUT SYSTEM

(71) Applicant: PreciPoint GmbH, Freising (DE)

(72) Inventor: Stephan Wienert, Lubben (DE)

(73) Assignee: PreciPoint GmbH, Freising (DE)

( * ) Notice: Subject to any disclaimer, the term of this patent is extended or adjusted under 35 U.S.C. 154(b) by 463 days.

(21) Appl. No.: 17/777,487

(22) PCT Filed: Nov. 13, 2020

(86) PCT No.: PCT/EP2020/082065
§ 371 (c)(1),
(2) Date: May 17, 2022

(87) PCT Pub. No.: WO2021/094540
PCT Pub. Date: May 20, 2021

(65) Prior Publication Data
US 2023/0207103 A1    Jun. 29, 2023

(30) Foreign Application Priority Data
Nov. 17, 2019 (EP) .................................. 19209611

(51) Int. Cl.
*G16H 30/20* (2018.01)
*G06F 3/01* (2006.01)
(Continued)

(52) U.S. Cl.
CPC ............. *G16H 30/20* (2018.01); *G06F 3/017* (2013.01); *G06F 3/04883* (2013.01); *G06F 3/14* (2013.01); *G06V 10/25* (2022.01)

(58) Field of Classification Search
CPC ........ G16H 30/20; G06V 10/25; G06F 3/017; G06F 3/04883; G06F 3/14
(Continued)

(56) References Cited

U.S. PATENT DOCUMENTS 8,463,741 B2 * 6/2013 Ehlke ..................... G16H 15/00
705/2
10,139,614 B2  11/2018 Saur
(Continued)

FOREIGN PATENT DOCUMENTS

DE  102012220195 B4  3/2021
WO  9938149 A1  7/1999
(Continued)

OTHER PUBLICATIONS

Anonymous: "Touchpad—Wikipedia", Oct. 2, 2019, pp. 1-5, XP093153018, Retrieved from the internet: URL: https://en.wikipedia.org/w/index.php? title=Touchpad&oldid=919278408.

*Primary Examiner* — Gabriel I Garcia
(74) *Attorney, Agent, or Firm* — Getz Balich LLC

(57) ABSTRACT

A method of determining and displaying an area of interest of a digital microscopic tissue image from a plurality of the same, the images jointly forming a patient-specific image record, includes: displaying an initial area of interest of a particular image on a primary screen; accepting touch gestures from the user on a touch-based input device positioned substantially horizontally at the desk; upon receiving a touch gesture from a first class of touch gestures, determining an updated area of interest within the particular image and displaying the updated area of interest of the particular image on the primary screen; and upon receiving a touch gesture from a second class of touch gestures, switching from the particular image to a different one of the images
(Continued)

and displaying an initial area of interest of said different one of the images on the primary screen.

13 Claims, 11 Drawing Sheets

(51) Int. Cl.
*G06F 3/04883* (2022.01)
*G06F 3/14* (2006.01)
*G06V 10/25* (2022.01)

(58) Field of Classification Search
USPC .......................................................... 382/128
See application file for complete search history.

(56) References Cited

U.S. PATENT DOCUMENTS

| | | | |
|---|---|---|---|
| 2007/0047785 A1* | 3/2007 | Jang | G06T 7/77 382/125 |
| 2009/0138800 A1 | 5/2009 | Anderson | |
| 2011/0013329 A1* | 1/2011 | Chishima | H02H 3/087 361/93.9 |
| 2014/0139541 A1 | 5/2014 | Willaert | |
| 2019/0252061 A1 | 8/2019 | Chang | |
| 2021/0018741 A1* | 1/2021 | Schwab | G02B 21/365 |

FOREIGN PATENT DOCUMENTS

| | | | | |
|---|---|---|---|---|
| WO | 2005114369 A2 | 12/2005 | | |
| WO | WO-2015122577 A1 * | 8/2015 | ......... | G06K 9/00013 |
| WO | 2018002776 A1 | 1/2018 | | |
| WO | 2019166266 A1 | 9/2019 | | |

* cited by examiner

METHOD OF DETERMINING AND DISPLAYING AN AREA OF INTEREST OF A DIGITAL MICROSCOPE TISSUE IMAGE, INPUT/OUTPUT SYSTEM FOR NAVIGATING A PATIENT-SPECIFIC IMAGE RECORD, AND WORK PLACE COMPRISING SUCH INPUT/OUTPUT SYSTEM

This application claims priority to PCT Patent Appln. No. PCT/EP2020/082065 filed Nov. 13, 2020, which claims priority EP Patent Appln. No. 19208611.3 filed Nov. 17, 2019, which are herein incorporated by reference.

BACKGROUND OF THE INVENTION

1. Technical Field

The present invention is in the field of medical microscopy. In particular, the present invention is in the field of methods and tools for making microscopic images available for analysis.

2. Background Information

In medical microscopy, various cuts of a tissue sample of a patient are generally analyzed by medical personnel. In the field of analog microscopy, the various cuts are provided on various slides. The various slides are commonly analyzed in sequence by a pathologist, who is manually placing them one-by-one on the table of an analog microscope for analysis. In the field of digital microscopy, the various cuts may be digitized by a digital microscope and may be stored as digital images in a folder of a file system of a computer. The pathologist may then open the digital images one-by-one for analysis, e.g. via common double-click commands on a mouse or the like. Both in the realm of analog microscopy and in the realm of digital microscopy, the working environments for pathologists or other medical personnel are not considered satisfactory in terms of allowing the pathologist to work at a high pace and in an ergonomic manner.

Accordingly, it would be beneficial to provide methods and systems that allow for an improved medical personnel interaction with their working environment and for an improved access to microscopic tissue images.

SUMMARY OF THE INVENTION

Exemplary embodiments of the invention include a method of determining and displaying an area of interest of a digital microscopic tissue image from a plurality of digital microscopic tissue images, the plurality of digital microscopic tissue images jointly forming a patient-specific image record, the method comprising: displaying an initial area of interest of a particular one of the plurality of digital microscopic tissue images on a primary screen, positioned in a forward viewing direction for a user sitting at a desk; accepting touch gestures from the user on a touch-based input device, such as a touch screen or a touch pad, the touch-based input device being positioned substantially horizontally at the desk; upon receiving a touch gesture from a first class of touch gestures, determining an updated area of interest within the particular one of the plurality of digital microscopic tissue images and displaying the updated area of interest of the particular one of the plurality of digital microscopic tissue images on the primary screen; and, upon receiving a touch gesture from a second class of touch gestures, switching from the particular one of the plurality of digital microscopic tissue images to a different one of the plurality of digital microscopic tissue images and displaying an initial area of interest of said different one of the plurality of digital microscopic tissue images on the primary screen.

Exemplary embodiments of the invention allow for medical personnel to navigate a patient-specific image record, having a plurality of digital microscopic tissue images, in a quick and ergonomic manner. By accepting two different classes of touch gestures, with the first class of touch gestures allowing for navigation within a particular digital microscopic tissue image and with the second class of touch gestures allowing for switching between different digital microscopic tissue images of the same patient, a quick and intuitive navigation through the patient-specific image record is facilitated. By accepting the touch gestures on a touch-based input device, being positioned substantially horizontally at the desk, and by displaying the areas of interest of the digital microscopic tissue images on a primary screen in a forward viewing direction of the user, an ergonomic de-coupling of image navigation on the one hand and image output on the other hand is facilitated. Performing touch gestures on a substantially horizontal touch-based input device may feel particularly intuitive for pathologists and other medical personnel, because they are used to small one-finger or two-finger displacement motions in a horizontal plane, when manually moving the table of an analog microscope for browsing through the different portions of a slide. With the data input being accepted on a substantially horizontal touch-based input device and the image output being provided in a forward viewing direction, the user may analyze patient records for extended periods of time, without putting undue burden on his/her body, such as on the back, on the shoulders, and/or on the arms. The described method allows for a particularly ergonomic work set-up for pathologists or other medical personnel.

The method comprises accepting touch gestures from the user on a touch-based input device. The term accepting means that the touch-based input device is in and on state or standby state, in which it is ready to detect touch gestures from the user. In other words, the term accepting touch gestures means that the touch-based input device is in a ready-to-detect/ready-to-receive state.

The method comprises accepting touch gestures from the user on a touch-based input device. In particular, the method comprises accepting a first class of touch gestures and a second class of touch gestures from the user on a touch-based input device. Both the first class of touch gestures and the second class of touch gestures are interpreted by the method as navigation commands within the patient-specific image record. The first class of touch gestures and the second class of touch gestures are fundamentally different in how they are interpreted by the method. While the first class of touch gestures is interpreted as navigation commands within a particular digital microscopic tissue image, the second class of touch gestures is interpreted as switching commands between different digital microscopic tissue images of the patient-specific image record. The particular touch gestures belonging to the first class and the particular touch gestures belonging to the second class may be defined in accordance with a convention applicable to the specific implementation of the method. The first class of touch gestures may comprise one or more touch gestures. Also, the second class of touch gestures may comprise one or more touch gestures.

The method comprises determining an updated area of interest within the particular one of the plurality of digital microscopic tissue images upon receiving a touch gesture from a first class of touch gestures. This means that, upon receiving any particular one of the first class of touch gestures on the touch-based input device, the method determines an updated area of interest within the particular one of the plurality of digital microscopic tissue images. The first class of touch gestures is mapped to a modification of the area of interest within the particular one of the plurality of digital microscopic tissue images.

The method comprises switching from the particular one of the plurality of digital microscopic tissue images to a different one of the plurality of digital microscopic tissue images upon receiving a touch gesture from a second class of touch gestures. This means that, upon receiving any particular one of the second class of touch gestures, the method switches from the particular one of the plurality of digital microscopic tissue images to a different one of the plurality of digital microscopic tissue images. The second class of touch gestures is interpreted as a switching command between different ones of the plurality of digital microscopic tissue images.

The method comprises displaying an initial area of interest of a particular one of the plurality of digital microscopic tissue images, displaying an updated area of interest within the particular one of the plurality of digital microscopic tissue images upon receiving a touch gesture from a first class of touch gestures, and displaying an initial area of interest of a different one of the plurality of digital microscopic tissue images upon receiving a touch gesture from a second class of touch gestures. The term initial area of interest of the particular one of the plurality of digital microscopic tissue images may refer to a starting point in the analysis of the patient-specific image record. However, it may also refer to the area of interest that is displayed on the primary screen at some point throughout the analysis of the patient-specific image record, with the ensuing method steps then being applied thereto. In other words, the initial area of interest of the particular one of the plurality of digital microscopic tissue images is the starting point of the described method steps, irrespective of whether this starting point coincides with the beginning of the analysis of the patient-specific image record or whether the starting point of the method relates to another point in time in the analysis of the patient-specific image record. The term updated area of interest within the particular one of the plurality of digital microscopic tissue images relates to a different portion of the particular one of the plurality of digital microscopic tissue images, as compared to said initial area of interest of the particular one of the plurality of digital microscopic tissue images. The term initial area of interest of the different one of the plurality of digital microscopic tissue images relates to an area of interest of a digital microscopic tissue image different from said particular one of the plurality of digital microscopic tissue images. While the term initial area of interest is used in two contexts, the initial area of interest of the particular one of the plurality of digital microscopic tissue images is different from the initial area of interest of the different one of the plurality of digital microscopic tissue images. In the context of the different one of the plurality of digital microscopic tissue images, the term initial area of interest is also used, because it relates to the initial display of the different one of the plurality of digital microscopic tissue images after the image switch. In general, the term area of interest may relate to the full image in question or to a portion of the image in question.

The method comprises switching from the particular one of the plurality of digital microscopic tissue images to a different one of the plurality of digital microscopic tissue images upon receiving a touch gesture from a second class of touch gestures. The term switching means that the different one of the plurality of digital microscopic tissue images is made the subject of ensuing operations. In particular, the different one of the plurality of digital microscopic tissue images is subject to the ensuing displaying on the primary screen. Also, the different one of the plurality of digital microscopic tissue images is made the subject of ensuing touch gestures from the first class of touch gestures, modifying the area of interest of said different one of the plurality of digital microscopic tissue images. In other words, switching to the different one of the plurality of digital microscopic tissue images makes said different one of the plurality of digital microscopic tissue images the input focus of the touch-based input device.

The method comprises displaying an initial area of interest of the different one of the plurality of digital microscopic tissue images on the primary screen. When displaying the initial area of interest of the different one of the plurality of digital microscopic tissue images, the initial area of interest of the particular one of the plurality of digital microscopic tissue images may be no longer displayed on the primary screen. In other words, the initial area of interest of the different one of the plurality of digital microscopic tissue images may replace the initial area of interest of the particular one of the plurality of digital microscopic tissue images on the primary screen. In general, the area of interest being displayed on the primary screen may be displayed over substantially the entire primary screen. The term substantially entire primary screen takes into account that other small screen elements, such as task bars, small preview windows for other digital microscopic tissue images, etc. may also be displayed. The other screen elements are smaller on the primary screen than the area of interest being displayed.

Exemplary embodiments of the invention allow for quickly and conveniently navigating a patient-specific image record. The patient-specific image record comprises a plurality of digital microscopic tissue images. This plurality of digital microscopic tissue images may show a plurality of cuts of one or more tissue samples taken from the patient. The term tissue may refer to any kind of substance taken from a patient, with the term patient being understood to refer to humans and animals. Images of tissue samples taken from a dead human body or from a dead animal are also considered as being taken from a patient. The term tissue encompasses all kinds of substances of a human or animal body, such as skin tissue, bone tissue, muscle tissue, organ tissue, brain tissue, etc. The plurality of digital microscopic tissue images may be the result of digitizing cuts of tissue samples with a digital microscope. The patient-specific image record may be part of a more comprehensive patient record, such as a patient record having a patient-specific image record and a patient-specific text-based record.

The primary screen is positioned in a forward viewing direction for a user, such as a pathologist or other medical personnel, sitting at the desk. The term forward viewing direction encompasses a straight-ahead forward viewing direction or an angled forward viewing direction in relation to an edge of the desk the user is sitting at. The term forward viewing direction may comprise all directions within an angle of +/−60° with respect to the straight-ahead forward viewing direction, in particular all directions within an angle of +/−45° with respect to a straight-ahead forward viewing direction. The straight-ahead forward viewing direction may be defined as the direction perpendicular to the edge of the desk the user is sitting at.

The touch-based input device is positioned substantially horizontally at the desk. In particular, an input plane of the touch-based input device may be positioned at an angle of less than 30°, in particular of less than 20°, further in particular of less than 10° with respect to the tabletop of the desk. The touch-based input device may be perceived as a structure substantially in alignment with the tabletop of the desk. The touch-based input device may be mounted to or integrated with the desk. In particular, the touch-based input device may be mounted to or integrated with the tabletop of the desk.

The touch-based input device may be a touch screen or a touch pad or another suitable touch-based input device, in particular a touch-based input device having a substantially planar input surface.

According to a further embodiment, the first class of touch gestures comprises at least one of a one-finger pan, a two-finger pinch, a two-finger stretch, and a two-finger rotational motion. In particular, the first class of touch gestures may comprise one or a subset or all of said touch gestures. The one-finger pan may be interpreted as a lateral motion command within said particular one of the plurality of digital microscopic tissue images. The two-finger pinch may be interpreted as a zoom out command within said particular one of the plurality of digital microscopic tissue images. The two-finger stretch may be interpreted as a zoom in command within said one of the plurality of digital microscopic tissue images. The two-finger rotational motion may be interpreted as a rotation command of said particular one of the plurality of digital microscopic tissue images. The terms two-finger pinch and two-finger stretch refer to a compressing/collapsing motion with two fingers on the one hand and to a spreading/expanding motion with two fingers on the other hand.

In a particular embodiment, the method comprises, in response to the one-finger pan, determining an updated area of interest that is laterally offset from the initial area of interest in the particular one of the plurality of digital microscopic tissue images. The method then displays said updated area of interest, which is laterally offset from the initial area of interest, on the primary screen. The updated area of interest may be displayed over the same extension of the primary screen as the previous display of the initial area of interest.

In a particular embodiment, the method comprises, in response to the two-finger pinch, determining an updated area of interest whose relative size with respect to the particular one of the plurality of digital microscopic tissue images is increased, as compared to the initial area of interest of the particular one of the plurality of digital microscopic tissue images. The method then displays said updated area of interest, which is zoomed out with respect to the initial area of interest, on the primary screen. The updated area of interest may be displayed over the same extension of the primary screen as the previous display of the initial area of interest.

In a particular embodiment, the method comprises, in response to the two-finger stretch, determining an updated area of interest whose relative size with respect to the particular one of the plurality of digital microscopic tissue images is reduced, as compared to the initial area of interest of the particular one of the plurality of digital microscopic tissue images. The method then displays said updated area of interest, which is zoomed in with respect to the initial area of interest, on the primary screen. The updated area of interest may be displayed over the same extension of the primary screen as the previous display of the initial area of interest.

In a particular embodiment, the method comprises, in response to the two-finger rotational motion, determining an updated area of interest that is rotated with respect to the initial area of interest in the particular one of the plurality of digital microscopic tissue images. The method then displays said updated area of interest, which is rotationally offset from the initial area of interest, on the primary screen. The updated area of interest may be displayed over the same extension of the primary screen as the previous display of the initial area of interest.

According to a further embodiment, the second class of touch gestures comprises at least one multi-finger pan. In particular, the second class of touch gestures may comprise at least one two-finger pan and/or at least one three-finger pan and/or at least one four-finger pan. Allowing a user to switch between different digital microscopic tissue images with multi-finger pans provides for a very intuitive, convenient, and quick way of browsing through the different digital microscopic tissue images of the patient-specific image record.

According to a further embodiment, the second class of touch gestures comprises a sideways multi-finger pan towards the left and a sideways multi-finger pan towards the right. In particular, the second class of touch gestures may comprise a sideways two-finger pan towards the left and a sideways two-finger pan towards the right. The sideways multi-finger pan towards the left may be interpreted as a command to switch to the next digital microscopic tissue image and the sideways multi-finger pan towards the right may be interpreted as a command to switch to the previous digital microscopic tissue image. The terms previous and next digital microscopic tissue image may refer to a predefined order of the plurality of digital microscopic tissue images of the patient-specific image record or may refer to a previous viewing sequence or to another kind of order of the plurality of digital microscopic tissue images. Instead of/in addition to the multi-finger pan towards the left and the multi-finger pan towards the right, upwards and downwards multi-finger pans are also possible. The provision of multi-finger pans for switching between different ones of the plurality of digital microscopic tissue images allows for an intuitive distinction between the second class of touch gestures and the first class of touch gestures, as laid out above.

According to a further embodiment, the method is carried out repeatedly. In particular, the method may comprise continuously accepting touch gestures from the user on the touch-based input device. For each newly received touch gesture from the user on the touch-based input device, the method may carry out one or more of the other method steps, depending on the particular touch gesture. For example, the displaying of the updated area of interest of the particular one of the plurality of digital microscopic tissue images or the displaying of an initial area of interest of a different one of the plurality of digital microscopic tissue images in a particular iteration of the method may be viewed as the displaying of a new initial area of interest in the step of displaying an initial area of interest of a particular one of the plurality of digital microscopic tissue images in the next iteration of the method. Subsequent touch gestures from the user may thus result in a sequence of determining updated areas of interest within a particular digital microscopic tissue image and/or switching between different ones of the plurality of digital microscopic tissue images.

According to a further embodiment, the touch-based input device is a secondary screen. In this way, the touch-based input device may not only act as an input device for touch gestures from a user, but also as an output device. The output capabilities of the secondary screen may beneficially interact with the input capabilities. In particular, the user may adapt the touch gestures to what is displayed on the secondary screen.

According to a further embodiment, the method further comprises: displaying an arrangement of previews of at least a subset of the plurality of digital microscopic tissue images on the touch-based input device; and, upon receiving a touch-based image selection command from the user, the touch-based image selection command indicating a selected one of the plurality of digital microscopic tissue images, using the selected one of the plurality of digital microscopic tissue images as said particular one of the plurality of digital microscopic tissue images for the step of displaying an initial area of interest of a particular one of the plurality of digital microscopic tissue images on the primary screen. In this way, the touch-based input device may be used as additional means for switching between different ones of the plurality of digital microscopic tissue images. Also, when starting the analysis of a patient-specific image record, the user may define via the touch-based image selection command which digital microscopic tissue images to start with. Accordingly, the method steps of displaying the arrangement of previews on the touch-based input device and using the selected one of the plurality of digital microscopic tissue images as said particular one of the plurality of digital microscopic tissue images may be carried out at the beginning of the analysis of the patient-specific image record. It is also possible that those method steps are carried out at an intermediate point in time during the analysis of the patient-specific image record, for example after entering a preview mode at some arbitrary point in time. The touch-based image selection command may be a tap on the preview of the digital microscopic tissue image to be selected or any other suitable touch-based command, singling out a particular one of the plurality of digital microscopic tissue images.

According to a further embodiment, the method comprises providing an image output on the secondary screen substantially corresponding to the area of interest displayed on the primary screen. In other words, the area of interest displayed on the primary screen may be substantially mirrored to the secondary screen. In this way, the user may receive additional support when carrying out touch gestures on the secondary screen. It is understood that the correspondence between the area of interest displayed on the primary screen and the image output on the secondary screen may be constrained by practical considerations, such as different width-to-height ratios of the primary screen and the secondary screen, the display of different task bars on the primary screen and the secondary screen, etc.

According to a further embodiment, said displaying of an initial area of interest of said different one of the plurality of digital microscopic tissue images comprises displaying a full view of said different one of the plurality of digital microscopic tissue images or a previously displayed area of interest of said different one of the plurality of digital microscopic tissue images on the primary screen. In this way, after switching from one digital microscopic tissue image to another, the method may either provide an overview as the initial area of interest or may provide an area of interest that has a high likelihood of being the area of interest the user wishes to see. The latter may in particular be beneficial, in case a user flips back and forth between two of the digital microscopic tissue images, e.g. for comparing digital microscopic tissue images of cuts being positioned in close vicinity to each other.

According to a further embodiment, the method further comprises displaying a patient-specific text-based record on a tertiary screen; providing a cursor on the tertiary screen and accepting cursor placement commands and data input into the patient-specific text-based record from at least one additional input device, such as from a mouse and/or from a keyboard; and, when receiving touch gestures from the user on the touch-based input device, maintaining a position of the cursor on the tertiary screen and/or upholding a readiness of accepting data input into the patient-specific text-based record from the at least one additional input device. In this way, the accepting of touch gestures on the touch-based input device and the interaction between those touch gestures and what is displayed on the primary screen does not interfere with the patient-specific text-based record, as displayed on the tertiary screen, being available for cursor placement commands and data input. From a user point of view, the particular one of the plurality of digital microscopic tissue images may be navigated and/or a switch between different digital microscopic tissue images may be carried out, and the patient-specific text-based record may continue to be available for further input, without having two re-place the cursor and/or without having two re-activate the patient-specific text-based record on the tertiary screen. In a particular implementation, upon receiving a touch gesture on the touch-based input device, the input focus may shift from the patient-specific text-based record to the area of interest window, displayed on the primary screen, and may shift immediately back to the patient-specific text-based record, after the response to the touch gesture has been performed. The shift of the input focus to the area of interest and back to the patient-specific text-based record may be carried out so quickly that it is not or barely noticeable to the user.

The terms secondary screen and tertiary screen are used for distinguishing these two screens. It is possible that the touch-based input device is embodied as the secondary screen, without the tertiary screen being present, and it is possible that the tertiary screen is present, without the touch-based input device being embodied as the secondary screen.

Exemplary embodiments of the invention further include a method of determining and displaying an area of interest of a digital microscopic tissue image from a plurality of digital microscopic tissue images, the plurality of digital microscopic tissue images jointly forming a patient-specific image record, the method comprising: displaying an initial area of interest of a particular one of the plurality of digital microscopic tissue images on a primary screen, positioned in a forward viewing direction for a user sitting at a desk; accepting touchless motion gestures from the user by a motion sensor, the motion sensor being directed towards a region at or above a tabletop of the desk; upon receiving a touchless motion gesture from a first class of touchless motion gestures, determining an updated area of interest within the particular one of the plurality of digital microscopic tissue images and displaying the updated area of interest of the particular one of the plurality of digital microscopic tissue images on the primary screen; and, upon receiving a touchless motion gesture from a second class of touchless motion gestures, switching from the particular one of the plurality of digital microscopic tissue images to a different one of the plurality of digital microscopic tissue images and displaying an initial area of interest of said different one of the plurality of digital microscopic tissue images on the primary screen. The accepting of touchless motion gestures by a motion sensor is an alternative solution to the accepting of touch gestures on a touch-based input device, as described above. With the motion sensor being directed towards a region at or above the tabletop of the desk, the present solution also allows for a quick, convenient, and ergonomic navigation of the patient-specific image record. The pathologist or other medical personnel may still provide gesture input, with the hand ergonomically positioned at the tabletop, and may still rest the hand on the tabletop in between gesture inputs. The additional features, modifications, and effects, described above with respect to the method comprising the accepting of touch gestures, apply to the method comprising the accepting of touchless motion gestures in an analogous manner, insofar as they are technically sensible in the context of a motion sensor detecting touchless motion gestures.

Exemplary embodiments of the invention further include an input/output system for navigating a patient-specific image record, comprising a plurality of digital microscopic tissue images, the system comprising: a primary screen for displaying an area of interest of a digital microscopic tissue image, the primary screen being configured to be positioned substantially vertically; and a touch-based input device for receiving touch gestures from a user, the touch-based input device being configured to be positioned substantially horizontally; wherein the input/output system is configured to: display an initial area of interest of a particular one of the plurality of digital microscopic tissue images on the primary screen; determine an updated area of interest within the particular one of the plurality of digital microscopic tissue images upon receiving a touch gesture from a first class of touch gestures and display the updated area of interest of the particular one of the plurality of digital microscopic tissue images on the primary screen; and switch from the particular one of the plurality of digital microscopic tissue images to a different one of the plurality of digital microscopic tissue images upon receiving a touch gesture from a second class of touch gestures and display an initial area of interest of said different one of the plurality of digital microscopic tissue images on the primary screen. The additional features, modifications, and effects, described above with respect to the method of determining and displaying an area of interest of a digital microscopic tissue image, apply to the input/output system for navigating a patient-specific image record in an analogous manner.

According to a further embodiment, the input/output system further comprises: a tertiary screen for displaying a patient-specific text-based record, with a cursor being provided on the tertiary screen during operation; and at least one additional input device, such as a mouse and/or a keyboard, for receiving cursor placement commands and data input into the patient-specific text-based record; wherein the input/output system is configured, when receiving touch gestures from the user on the touch-based input device, to maintain a position of the cursor on the tertiary screen and/or to uphold a readiness of accepting data input into the patient-specific text-based record from the at least one additional input device.

Exemplary embodiments of the invention further include an input/output system for navigating a patient-specific image record, comprising a plurality of digital microscopic tissue images, the system comprising: a primary screen for displaying an area of interest of a digital microscopic tissue image, the primary screen being configured to be positioned substantially vertically; and a motion sensor for receiving touchless motion gestures from a user, the motion sensor being configured to detect touchless motion gestures in a substantially horizontal plane; wherein the input/output system is configured to: display an initial area of interest of a particular one of the plurality of digital microscopic tissue images on the primary screen; determine an updated area of interest within the particular one of the plurality of digital microscopic tissue images upon receiving a touchless motion gesture from a first class of touchless motion gestures and display the updated area of interest of the particular one of the plurality of digital microscopic tissue images on the primary screen; and switch from the particular one of the plurality of digital microscopic tissue images to a different one of the plurality of digital microscopic tissue images upon receiving a touchless motion gesture from a second class of touchless motion gestures and display an initial area of interest of said different one of the plurality of digital microscopic tissue images on the primary screen. The additional features, modifications, and effects, described above with respect to the method of determining and displaying an area of interest of a digital microscopic tissue image, apply to the input/output system for navigating a patient-specific image record in an analogous manner.

According to a further embodiment, the input/output system further comprises: a tertiary screen for displaying a patient-specific text-based record, with a cursor being provided on the tertiary screen during operation; and at least one additional input device, such as a mouse and/or a keyboard, for receiving cursor placement commands and data input into the patient-specific text-based record; wherein the input/output system is configured, when receiving touchless motion gestures from the user by the motion sensor, to maintain a position of the cursor on the tertiary screen and/or to uphold a readiness of accepting data input into the patient-specific text-based record from the at least one additional input device.

Exemplary embodiments of the invention further include a work place for a medical personnel user, such as a doctor or a pathologist or a medical assistant or a nurse, the work place comprising: a desk; and an input/output system in accordance with any of the embodiments described above; wherein the primary screen is placed on the desk in a forward viewing direction of the user; and wherein the touch-based input device is mounted to or integrated with the desk and is positioned substantially horizontally at the desk. The additional features, modifications, and effects, described above with respect to the method of determining and displaying an area of interest of a digital microscopic tissue image and with respect to the input/output system for navigating a patient-specific image record, apply to the work place in an analogous manner.

Exemplary embodiments of the invention further include a work place for a medical personnel user, such as a doctor or a pathologist or a medical assistant or a nurse, the work place comprising: a desk; and an input/output system in accordance with any of the embodiments described above; wherein the primary screen is placed on the desk in a forward viewing direction of the user; and wherein the motion sensor is directed towards a region at or above a tabletop of the desk. The additional features, modifications, and effects, described above with respect to the method of determining and displaying an area of interest of a digital microscopic tissue image and with respect to the input/output system for navigating a patient-specific image record, apply to the work place in an analogous manner.

Exemplary embodiments of the invention further comprise a computer program or a computer program product which comprises program instructions which, when executed on a data processing system, perform a method of determining and displaying an area of interest of a digital microscopic tissue image form a plurality of digital microscopic tissue images according to any of the embodiments described above. In this regard, the individual steps of the method can be initiated by the program instructions and executed by other components or executed in the data processing system itself.

Exemplary embodiments of the invention further include a method of determining and displaying areas of interest of a subset of a plurality of digital microscopic tissue images, the plurality of digital microscopic tissue images jointly forming a patient-specific image record, the method comprising: displaying a first initial area of interest of a first digital microscopic tissue image of the plurality of digital microscopic tissue images and a second initial area of interest of a second digital microscopic tissue image of the plurality of digital microscopic tissue images on a primary screen, positioned in a forward viewing direction for a user sitting at a desk; providing an input focus for a particular one of the first digital microscopic tissue image and the second digital microscopic tissue image; accepting touch gestures from the user on a touch-based input device, such as a touch screen or a touch pad, the touch-based input device being positioned substantially horizontally at the desk; upon receiving a touch gesture from a first class of touch gestures, determining an updated area of interest within the particular one of the first and second digital microscopic tissue images and displaying the updated area of interest of the particular one of the first and second digital microscopic tissue images on the primary screen; and, upon receiving a touch gesture from a second class of touch gestures, switching the input focus from the particular one of the first and second digital microscopic tissue images to the other one of the first and second digital microscopic tissue image.

The subset may be any subset of the plurality of digital microscopic tissue images. The subset may comprise two or more or all of the plurality of digital microscopic tissue images. The terms first digital microscopic tissue image and second digital microscopic tissue image are used for differentiating between two different digital microscopic tissue images of the subset of digital microscopic tissue images. The first and second digital microscopic tissue images may be arbitrary ones of the subset of digital microscopic tissue images. In the case of more than two initial areas of interest, belonging to more than two digital microscopic tissue images, being displayed on the primary screen, the input focus may be switched to any of the digital microscopic tissue images of the subset not having the input focus. The step of providing an input focus means that one of the displayed subset of the plurality of digital microscopic tissue images has the input focus. The input focus may be newly assigned or may be carried over from a previous iteration of the method. The displaying of the updated area of interest may include displaying the updated area of interest at the same position and/or with the same extension on the primary screen as the initial area of interest of the particular one of the first and second digital microscopic tissue images.

The additional features, modifications, and effects, described above with respect to the method of determining and displaying an area of interest of a digital microscopic tissue image from a plurality of digital microscopic tissue images, apply to the method of determining and displaying areas of interest of a subset of a plurality of digital microscopic tissue images in an analogous manner.

Exemplary embodiments of the invention further include a method of determining and displaying areas of interest of a subset of a plurality of digital microscopic tissue images, the plurality of digital microscopic tissue images jointly forming a patient-specific image record, the method comprising: displaying a first initial area of interest of a first digital microscopic tissue image of the plurality of digital microscopic tissue images and a second initial area of interest of a second digital microscopic tissue image of the plurality of digital microscopic tissue images on a primary screen, positioned in a forward viewing direction for a user sitting at a desk; providing an input focus for a particular one of the first digital microscopic tissue image and the second digital microscopic tissue image; accepting touchless motion gestures from the user by a motion sensor, the motion sensor being directed towards a region at or above a tabletop of the desk; upon receiving a touchless motion gesture from a first class of touchless motion gestures, determining an updated area of interest within the particular one of the first and second digital microscopic tissue images and displaying the updated area of interest of the particular one of the first and second digital microscopic tissue images on the primary screen; and, upon receiving a touchless motion gesture from a second class of touchless motion gestures, switching the input focus from the particular one of the first and second digital microscopic tissue images to the other one of the first and second digital microscopic tissue image. The additional features, modifications, and effects, described above with respect to the method of determining and displaying an area of interest of a digital microscopic tissue image from a plurality of digital microscopic tissue images and with respect to the method of displaying areas of interest of a subset of a plurality of digital microscopic tissue images, apply to the method of determining and displaying areas of interest of a subset of a plurality of digital microscopic tissue images, comprising the accepting of touchless motion gestures, in an analogous manner.

Exemplary embodiments of the invention further include an input/output system for navigating a patient-specific image record, comprising a plurality of digital microscopic tissue images, the system comprising: a primary screen for displaying areas of interest of a subset of a plurality of digital microscopic tissue images, the primary screen being configured to be positioned substantially vertically; and a touch-based input device for receiving touch gestures from a user, the touch-based input device being configured to be positioned substantially horizontally; wherein the input/output system is configured to: display a first initial area of interest of a first digital microscopic tissue image of the plurality of digital microscopic tissue images and a second initial area of interest of a second digital microscopic tissue image of the plurality of digital microscopic tissue images on the primary screen; provide an input focus for a particular one of the first digital microscopic tissue image and the second digital microscopic tissue image; determine an updated area of interest within the particular one of the first and second digital microscopic tissue images upon receiving a touch gesture from a first class of touch gestures and display the updated area of interest of the particular one of the first and second digital microscopic tissue images on the primary screen; and switch the input focus from the particular one of the first and second digital microscopic tissue images to the other one of the first and second digital microscopic tissue images upon receiving a touch gesture from a second class of touch gestures. The additional features, modifications, and effects, described above with respect to other embodiments of an input/output system for navigating a patient-specific record and with respect to the method of determining and displaying areas of interest of a subset of a plurality of digital microscopic tissue images, apply to the present input/output system for navigating a patient-specific image record in an analogous manner.

Exemplary embodiments of the invention further include an input/output system for navigating a patient-specific image record, comprising a plurality of digital microscopic tissue images, the system comprising: a primary screen for displaying areas of interest of a subset of a plurality of digital microscopic tissue images, the primary screen being configured to be positioned substantially vertically; and a motion sensor for receiving touchless motion gestures from a user, the motion sensor being configured to detect touchless motion gestures in a substantially horizontal plane; wherein the input/output system is configured to: display a first initial area of interest of a first digital microscopic tissue image of the plurality of digital microscopic tissue images and a second initial area of interest of a second digital microscopic tissue image of the plurality of digital microscopic tissue images on the primary screen; provide an input focus for a particular one of the first digital microscopic tissue image and the second digital microscopic tissue image; determine an updated area of interest within the particular one of the first and second digital microscopic tissue images upon receiving a touchless motion gesture from a first class of touchless motion gestures and display the updated area of interest of the particular one of the first and second digital microscopic tissue images on the primary screen; and switch the input focus from the particular one of the first and second digital microscopic tissue images to the other one of the first and second digital microscopic tissue images upon receiving a touchless motion gesture from a second class of touchless motion gestures. The additional features, modifications, and effects, described above with respect to other embodiments of an input/output system for navigating a patient-specific record and with respect to the method of determining and displaying areas of interest of a subset of a plurality of digital microscopic tissue images, apply to the present input/output system for navigating a patient-specific image record in an analogous manner.

Exemplary embodiments of the invention further include a work place for a medical personnel user, such as a doctor or a pathologist or a medical assistant or a nurse, the work place comprising: a desk; and an input/output system in accordance with any of the embodiments described in the preceding two paragraphs. The additional features, modifications, and effects, described above with respect to other embodiments of a work place, apply to the present work place in an analogous manner.

Exemplary embodiments of the invention further comprise a computer program or a computer program product which comprises program instructions which, when executed on a data processing system, perform a method of determining and displaying areas of interest of a subset of a plurality of digital microscopic tissue images according to any of the embodiments described above. In this regard, the individual steps of the method can be initiated by the program instructions and executed by other components or executed in the data processing system itself.

BRIEF DESCRIPTION OF THE DRAWINGS

Further exemplary embodiments of the invention will be described below with respect to the accompanying drawings, wherein.

DETAILED DESCRIPTION OF THE INVENTION

Figure 1:
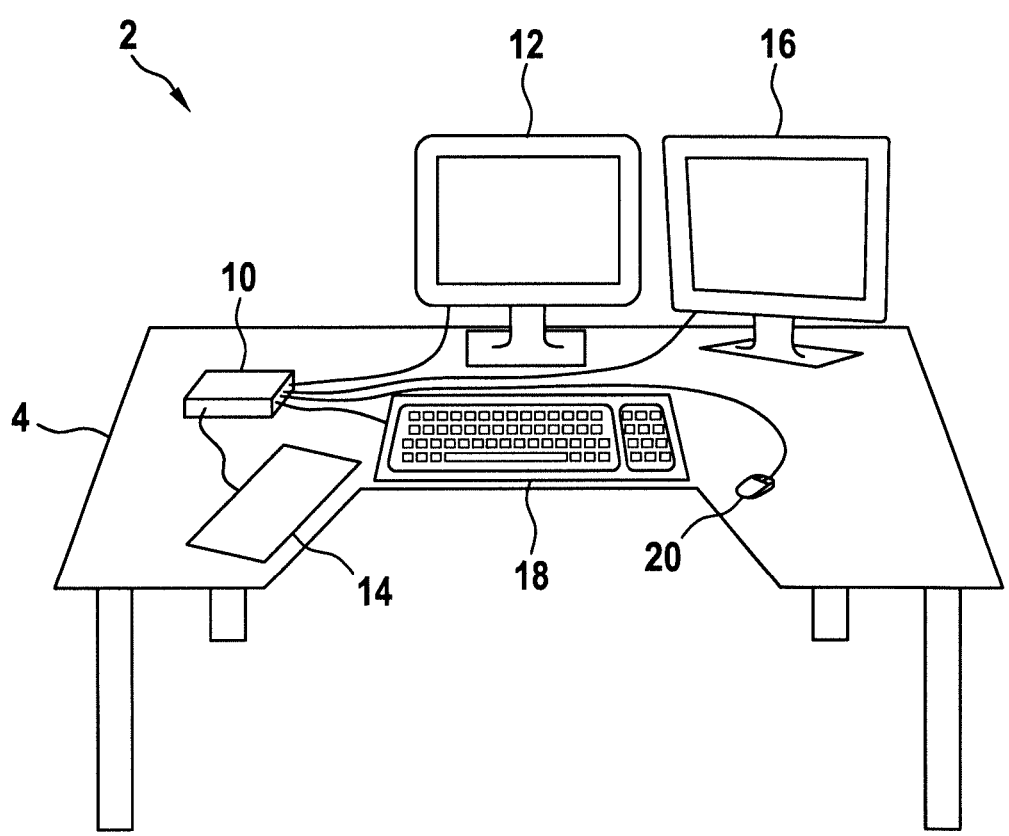
FIG. 1 shows a work place in accordance with an exemplary embodiment of the invention in a perspective view, the work place being equipped with an input/output system in accordance with an exemplary embodiment of the invention and the work place providing an environment for a method of determining and displaying an area of interest of a digital microscopic tissue image in accordance with an exemplary embodiment of the invention.

FIG. 1 shows a work place 2 in accordance with an exemplary embodiment of the invention in a perspective view. The work place 2 has a desk 4, at which a user, such as a pathologist or other medical personnel, may sit. In the exemplary embodiment of FIG. 1, the desk 4 has a cutout, such that a user, when sitting in or at said cutout, has a cockpit-like feeling and has easy access to various devices.

A number of input devices and output devices are arranged on or integrated with the desk 4. In particular, a touch screen 14 is arranged on the left side of the cutout of the desk 4, a keyboard 18 is arranged at the center of the cutout of the desk 4, and a mouse 20 is arranged to the right of the cutout of the desk 4. In this way, the user has easy access to the input devices touch screen 14, keyboard 18 and mouse 20, such that a convenient and ergonomic working environment is facilitated. A primary screen 12 is arranged in a straight-ahead forward viewing direction of a user sitting in the cutout of the desk 4. The touch screen 14 acts as a secondary screen, and a tertiary screen 16 is arranged in a forward viewing direction to the right of the primary screen 12. It is understood that the input devices touch screen 14, keyboard 18, and mouse 20 may be arranged in a modified manner. For example, the touch screen 14 and the mouse 20 may be interchanged. Also, the primary screen 12 and the tertiary screen 16 may be arranged differently, such as in a symmetrical manner, both being offset from the straight-ahead forward viewing direction of the user.

The primary screen 12, the touch screen 14, the tertiary screen 16, the keyboard 18, and the mouse 20 are connected to a computer 10, which is depicted as a box, sitting on the desk 4. The computer 10 may also be a tower-type computer, placed underneath the desk 4, or any other suitable kind of computer.

The computer 10, the primary screen 12, the touch screen 14, the tertiary screen 16, the keyboard 18, and the mouse 20 form an input/output system for navigating a patient-specific image record in accordance with an exemplary embodiment of the invention. Further, said components provide the environment for carrying out a method of determining and displaying an area of interest of a digital microscopic tissue image in accordance with an exemplary embodiment of the invention. The input devices touch screen 14, keyboard 18, and mouse 20 provide input data to the computer 10. The computer 10 provides output data to the primary screen 12, the touch screen 14, acting as a secondary screen, and the tertiary screen 16. The computer 10 has a memory for storing data and computing capacities for running software programs and for making the other components of the input/output system interact. The computer 10 is an exemplary data processing system.

In the exemplary embodiment of FIG. 1, the computer 10 stores at least one patient record that comprises a patient-specific image record and a patient-specific text-based record. The patient-specific image record comprises a plurality of digital microscopic tissue images, as will be discussed and illustrated below. The patient record may be stored locally in the computer 10 or may be accessed on a remote device, such as a remote server, via the computer 10. The computer 10 may be connected to other computers, servers, etc. via a network connection, such as via an internet connection.

In operation, the computer 10 may control the primary screen 12 to display an area of interest of a digital microscopic tissue image from a plurality of digital microscopic tissue images of the patient-specific image record. Further, the computer may control the tertiary screen 16 to display the patient-specific text-based record or parts thereof. In this way, the user, such as a doctor, pathologist, medical assistant, nurse, etc., may work with the patient-specific image record and the patient-specific text-based record simultaneously in the work place 2. The plurality of digital microscopic tissue images of the patient-specific image record may have been generated by digitizing tissue cuts via a digital microscope or may have been provided in another suitable manner. The plurality of digital microscopic tissue images may also be the result of post-processing steps and/or selection steps and/or image organizing steps, carried out after digitizing tissue samples with a digital microscope.

With the touch screen 14, the user of the workplace 2 may navigate the patient-specific image record in a quick and convenient manner, while working at a highly ergonomic work place 2. In particular, the input/output system in accordance with an exemplary embodiment of the invention and the method of determining and displaying an area of interest of a digital microscopic tissue image in accordance with an exemplary embodiment of the invention provide for particularly quick access to the parts of interest of the patient-specific image record.

The work place 2/the input/output system of FIG. 1 may comprise further devices. For example, other kinds of input devices may be provided. Also, a digital microscope may be coupled to the computer 10. In this way, the digitizing of cuts of tissue samples may be carried out in the work place 2.

FIG. 2 illustrates a part of a method of determining and displaying an area of interest of a digital microscopic tissue image in accordance with an exemplary embodiment of the invention. In particular, FIG. 2 illustrates a part of such a method that may be carried out at the beginning of analyzing the patient-specific image record.

Figure 2A:
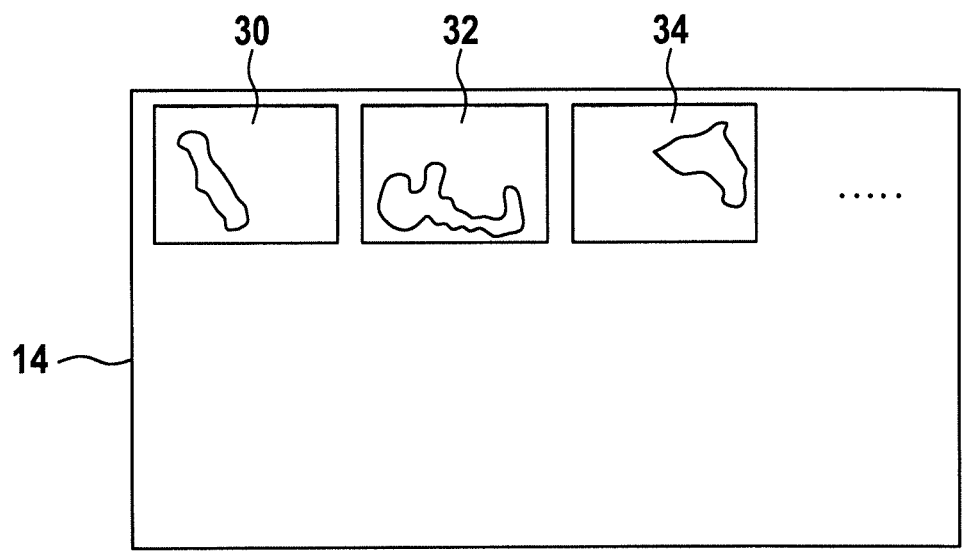
FIGS. 2A-2C illustrate an example of selecting a particular digital microscopic tissue image, as employed in a method of determining and displaying an area of interest of a digital microscopic tissue image in accordance with an exemplary embodiment of the invention.

The analysis of the patient-specific image record may begin with the display of previews of the plurality of digital microscopic tissue images of the patient-specific image record on the touch screen 14. In FIG. 2A, three exemplary digital microscopic tissue images 30, 32, 34 are depicted, arranged next to each other on the touch screen 14. The first digital microscopic tissue image 30, the second digital microscopic tissue image 32, and the third digital microscopic tissue image 34 belong to the same patient-specific image record. In other words, they are all digitized images of cuts of one or more tissue samples taken from one specific patient. The dots on the right of the touch screen 14 indicate that the patient-specific image record may contain additional digital microscopic tissue images. The arrangement of the previews of the digital microscopic tissue images 30, 32, 34 on the touch screen 14 allows the user to select a particular one of the digital microscopic tissue images, in order to start the analysis of the patient-specific image record.

Figure 2B:
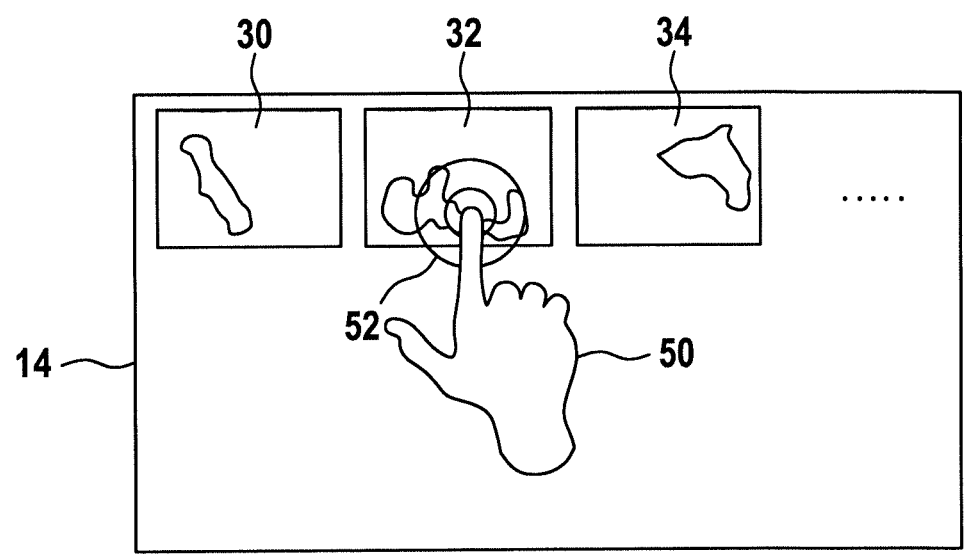

In FIG. 2B, a user selection of the second digital microscopic tissue image 32 as a starting point for the analysis is illustrated. In the exemplary embodiment of FIG. 2, a user tap on the preview of the second digital microscopic tissue image 32 is indicated via a hand 50, whose index finger taps on the touch screen 14. The tap on the touch screen 14 is illustrated by two concentric circles 52. The tap on the touch screen 14 is a touch-based image selection command for selecting the second digital microscopic tissue image 32.

As a result of the selection of the second digital microscopic tissue image 32, a full view of the second digital microscopic tissue image 32 is depicted on the primary screen 12. In particular, the full view of the second digital microscopic tissue image 32 forms the initial area of interest 80 of the particular selected digital microscopic tissue image, which is displayed on the primary screen 12, as illustrated in FIG. 2C.

Figure 2C:
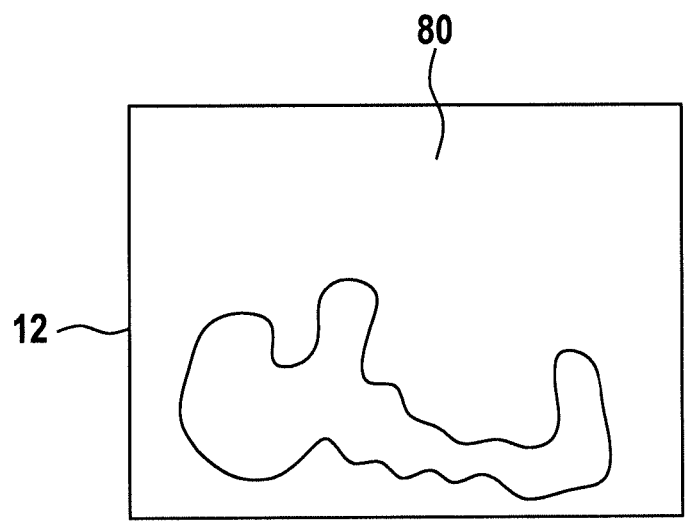
Figure 3A:
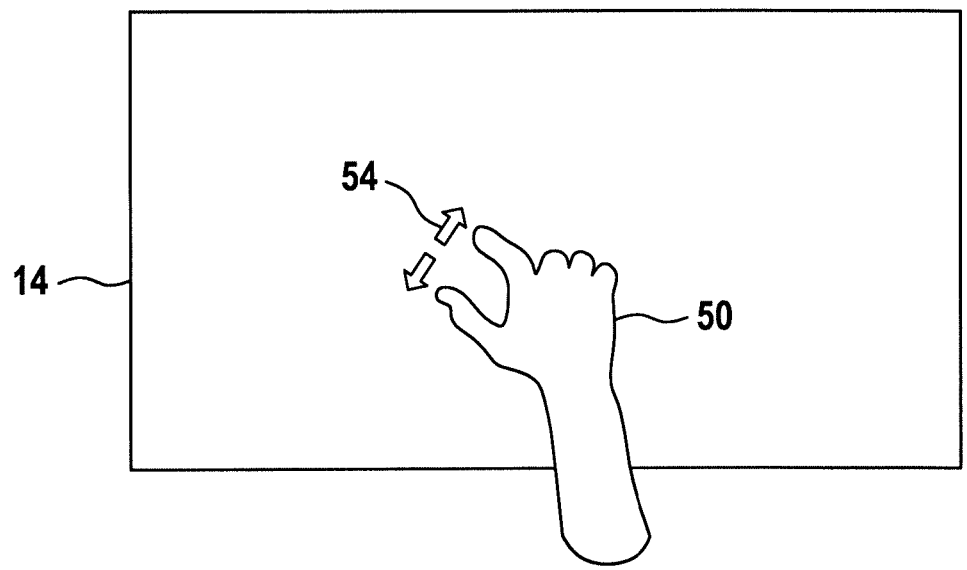
FIGS. 3A-3B, 4A-4B, and 5A-5B illustrate examples of determining updated areas of interest within a particular digital microscopic tissue image, as employed in a method of determining and displaying an area of interest of a digital microscopic tissue image in accordance with an exemplary embodiment of the invention.

FIG. 3 illustrates exemplary steps of a method of determining and displaying an area of interest of a digital microscopic tissue image in accordance with an exemplary embodiment of the invention. In particular, FIG. 3 illustrates an example of navigating within the particular one of the plurality of digital microscopic tissue images. The method steps, illustrated in FIG. 3, start from the display of the initial area of interest 80 on the primary screen 12, as illustrated in FIG. 2C. FIG. 3A illustrates that the touch screen 14 receives a two-finger stretch touch gesture 54 from a user. This is illustrated in FIG. 3A by the thumb and the index finger of hand 50 performing a spreading/expanding motion. The two-finger stretch gesture 54 is indicated with two arrows pointing away from each other.

The two-finger stretch touch gesture 54 is part of a first class of touch gestures, which are commands for navigating within the particular one of the plurality of digital microscopic tissue images displayed on the primary screen 12. The two-finger stretch touch gesture 54 is in particular interpreted as a zoom in command with respect to the area of interest 80, depicted on the primary screen 12.

Figure 3B:
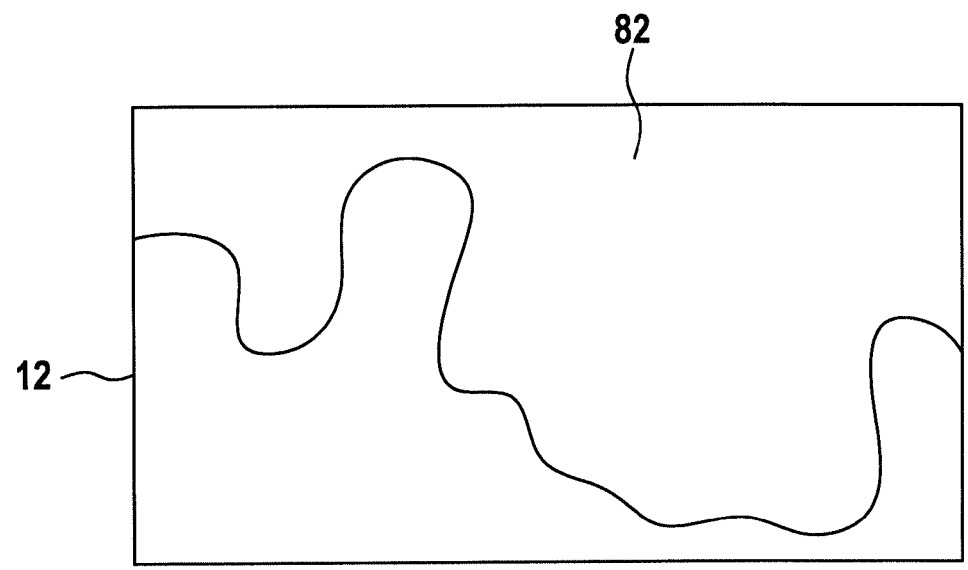

FIG. 3B illustrates an updated area of interest 82, which is the result of the zoom in command with respect to the initial area of interest 80, illustrated in FIG. 2C. Said updated area of interest 82 is then displayed on the primary screen 12, as illustrated in FIG. 3B. The updated area of interest 82 is a smaller portion of the second digital microscopic image 32, as compared to the initial area of interest 80.

A two-finger pinch touch gesture is another example of a touch gesture from the first class of touch gestures. The two-finger pinch touch gesture may be carried out by bringing the thumb and the index finger of the hand closer together, i.e. by carrying out a compressing/collapsing motion with the thumb and the index finger. The two-finger pinch touch gesture is interpreted as a zoom out command, resulting in the updated area of interest being a larger portion of the particular digital microscopic image, as compared to the initial area of interest. The two-finger pinch touch gesture is not shown in the Figs., but may be easily envisioned by having the arrows of FIG. 3A pointing towards each other.

FIG. 4 illustrates exemplary steps of a method of determining and displaying an area of interest of a digital microscopic tissue image in accordance with an exemplary embodiment of the invention. In particular, FIG. 4 illustrates an example of navigating within the particular one of the plurality of digital microscopic tissue images. The method steps, illustrated in FIG. 4, start from the display of the area of interest 82 on the primary screen 12, as illustrated in FIG. 3B. While the area of interest 82 has been referred to as updated area of interest 82 in the context of FIG. 3B, because it is the result of the zoom in touch gesture of FIG. 3A, the area of interest 82 is the initial area of interest for the iteration of the method illustrated in FIG. 4.

Figure 4A:
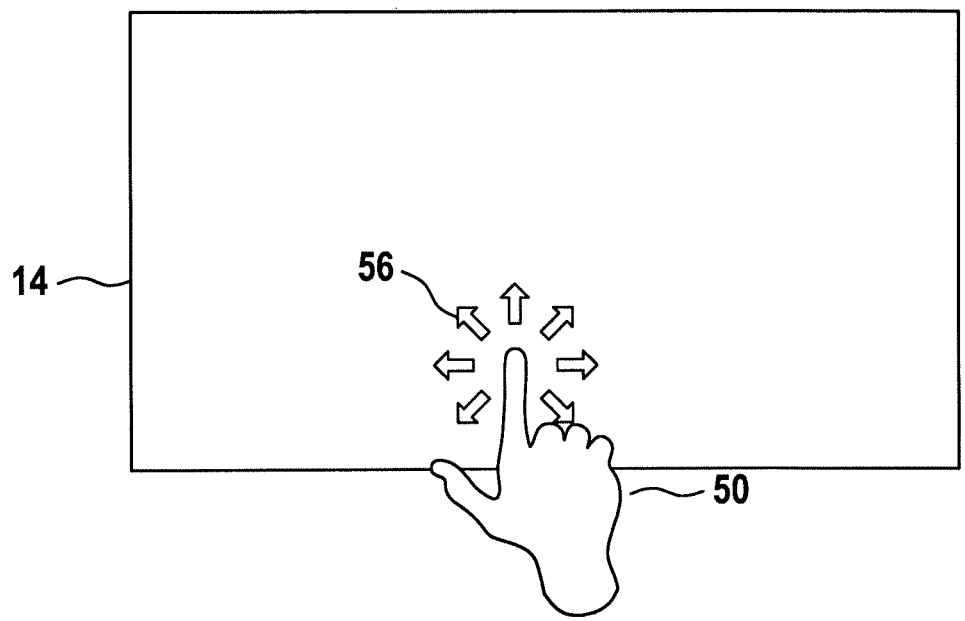

FIG. 4A illustrates that the touch screen 14 receives a one-finger pan gesture 56 from a user. This is illustrated in FIG. 4A by the index finger of the hand 50 performing a lateral motion on the touch screen 14. The one-finger pan gesture 56 is indicated with multiple arrows pointing away from the index finger in different directions, the multiple arrows illustrating that the one-finger pan may be carried out in different directions. For illustrative purposes, a one-finger pan in the left direction is assumed as an example of the one-finger pan gesture in the context of FIG. 4.

The one-finger pan touch gesture 56 is also part of the first class of touch gestures, which are commands for navigating within the particular one of the plurality of digital microscopic tissue images displayed on the primary screen 12. The one-finger pan touch gesture 56 is in particular interpreted as a lateral motion command with respect to the area of interest 82, which is the initial area of interest in the context of FIG. 4, depicted on the primary screen 12.

Figure 4B:
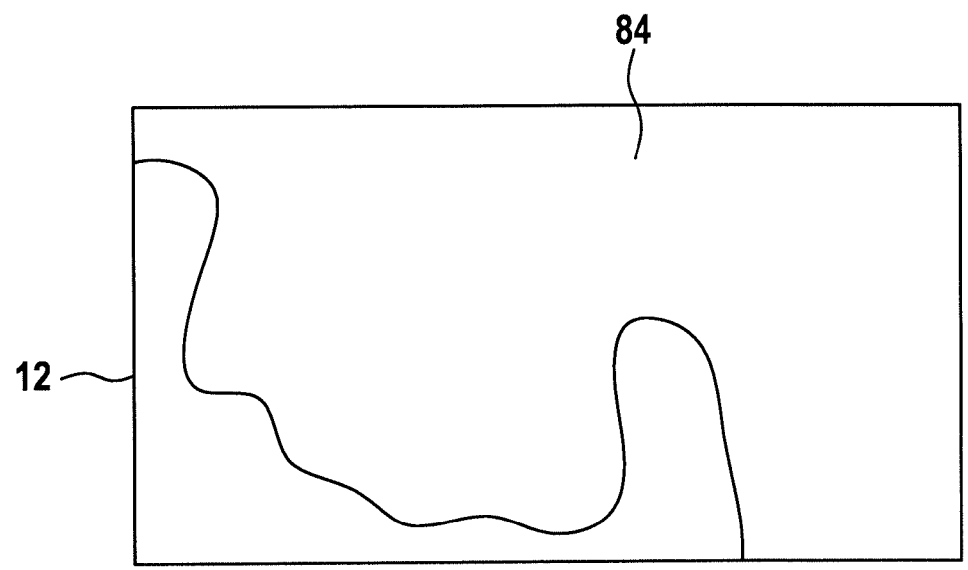

FIG. 4B illustrates an updated area of interest 84, which is the result of the lateral motion command with respect to the initial area of interest 82, illustrated in FIG. 3B. Said updated area of interest 84 is then displayed on the primary screen 12, as illustrated in FIG. 4B. It can be seen from the comparison of FIG. 3B and FIG. 4B that the image features of the depicted portion of the second digital microscopic tissue image 32 have been moved to the left.

FIG. 5 illustrates exemplary steps of a method of determining and displaying an area of interest of a digital microscopic tissue image in accordance with an exemplary embodiment of the invention. In particular, FIG. 5 illustrates an example of navigating within the particular one of the plurality of digital microscopic tissue images. The method steps, illustrated in FIG. 5, start from the display of the area of interest 82 on the primary screen 12, as illustrated in FIG. 3B. While the area of interest 82 has been referred to as updated area of interest 82 in the context of FIG. 3B, because it is the result of the zoom in touch gesture of FIG. 3A, the area of interest 82 is the initial area of interest for the iteration of the method illustrated in FIG. 5.

Figure 5A:
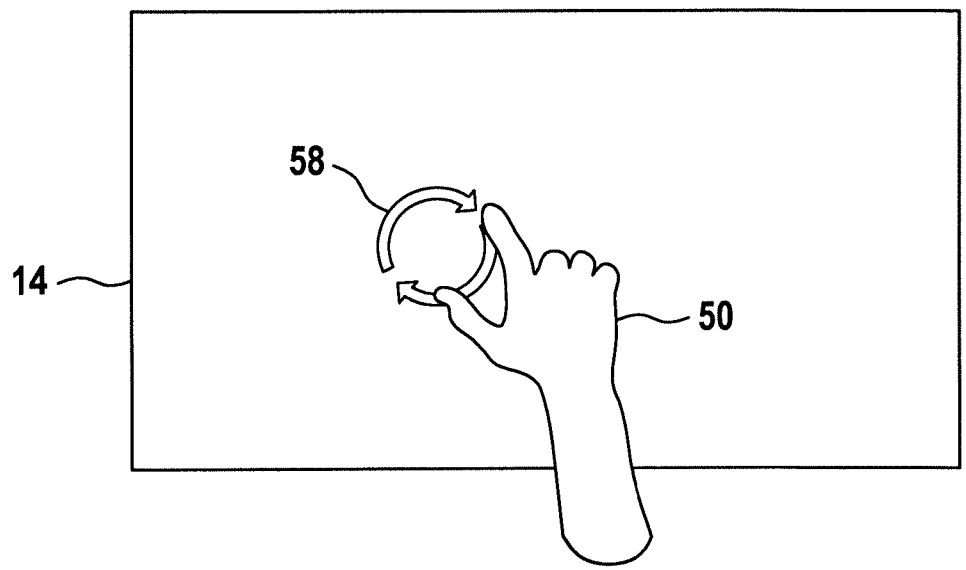

FIG. 5A illustrates that the touch screen 14 receives a two-finger rotational motion gesture 58 from a user. This is illustrated in FIG. 5A by the thumb and the index finger of the hand 50 jointly rotating on the touch screen 14. The two-finger rotational motion gesture 58 is indicated with two semi-circular arrows. For illustrative purposes, a two-finger rotational motion gesture 58 in the clockwise direction is assumed as an example of the two-finger rotational motion gesture in the context of FIG. 5.

The two-finger rotational motion gesture 58 is also part of the first class of touch gestures, which are commands for navigating within the particular one of the plurality of digital microscopic tissue images displayed on the primary screen 12. The two-finger rotational motion gesture 58 is in particular interpreted as a rotation command with respect to the area of interest 82, which is the initial area of interest in the context of FIG. 5, depicted on the primary screen 12.

Figure 5B:
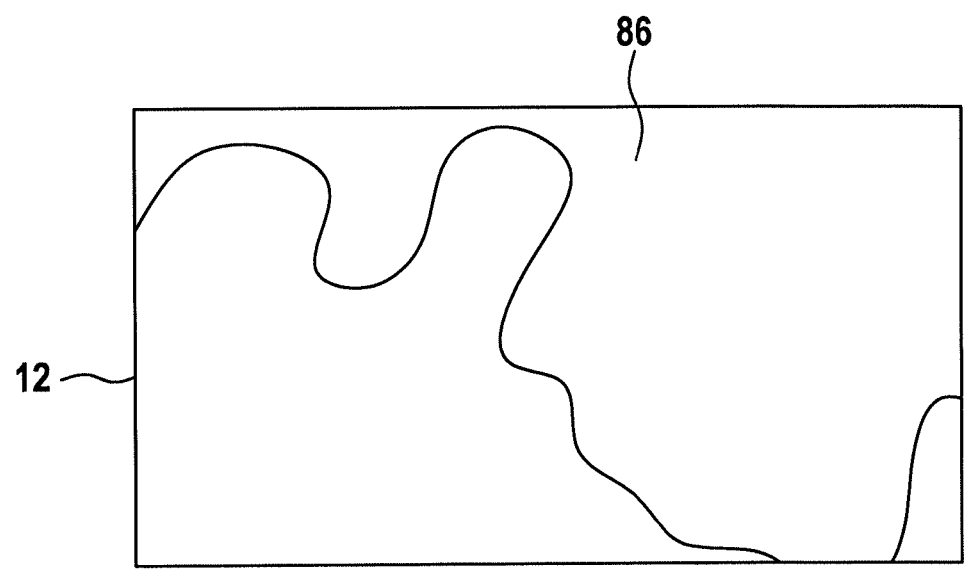

FIG. 5B illustrates an updated area of interest 86, which is the result of the rotation command with respect to the initial area of interest 82, illustrated in FIG. 3B. Said updated area of interest 86 is then displayed on the primary screen 12, as illustrated in FIG. 5B. It can be seen from the comparison of FIG. 3B and FIG. 5B that the image features of the depicted portion of the second digital microscopic tissue image 32 have been rotated clockwise.

A two-finger rotational motion gesture in the counter-clockwise direction may work in an analogous manner. Such two-finger rotational motion gesture in the counter-clockwise direction is also part of the first class of touch gestures.

FIG. 6 illustrates exemplary steps of a method of determining and displaying an area of interest of a digital microscopic tissue image in accordance with an exemplary embodiment of the invention. In particular, FIG. 6 illustrates an example of switching from a particular one of the plurality of digital microscopic tissue images to a different one of the plurality of digital microscopic tissue images. The method steps, illustrated in FIG. 6, may start from any area of interest of the second digital microscopic tissue image 32, such as from the display of any of the areas of interest 80, 82, 84, 86 on the primary screen 12, as depicted in FIGS. 2C, 3B, 4B, and 5B.

Figure 6A:
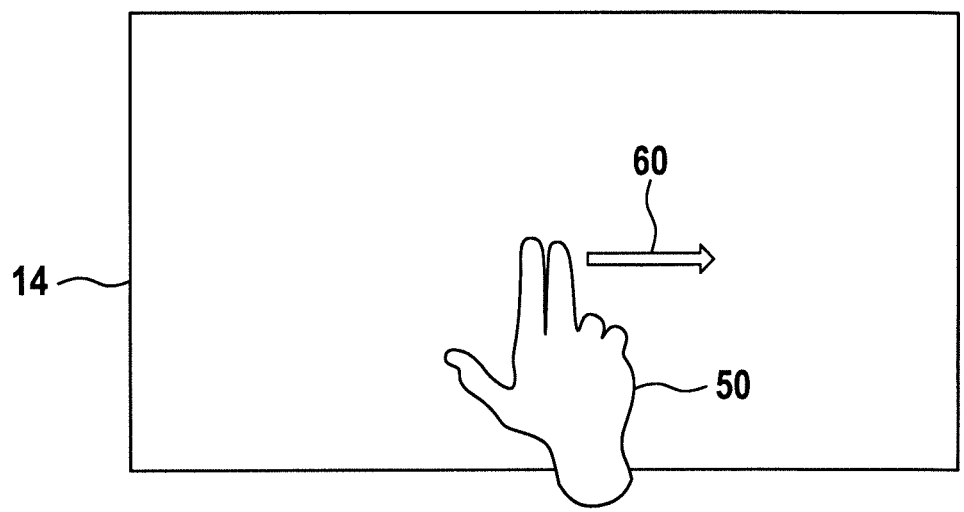
FIGS. 6A-6B and 7A-7B illustrate examples of switching from a particular digital microscopic tissue image to a different digital microscopic tissue image, as employed in a method of determining and displaying an area of interest of a digital microscopic tissue image in accordance with an exemplary embodiment of the invention.

FIG. 6A illustrates that the touch screen 14 receives a sideways two-finger pan gesture 60 towards the right from a user. This is illustrated in FIG. 6A by the index finger and the middle finger of the hand 50 performing a lateral motion on the touch screen 14 towards the right. The two-finger pan gesture 60 is indicated with an arrow pointing towards the right from the index and middle fingers of the hand 50.

The two-finger pan gesture 60 is part of a second class of touch gestures, which are commands for switching from a particular one of the plurality of digital microscopic tissue images to a different one of the plurality of digital microscopic tissue images. The two-finger pan touch gesture 60 towards the right is in particular interpreted as a command to switch to a previous one of the plurality of digital microscopic tissue images. In the case of FIG. 6, the two-finger pan touch gesture 60 towards the right is interpreted as a command to switch to the first digital microscopic tissue image 30.

Figure 6B:
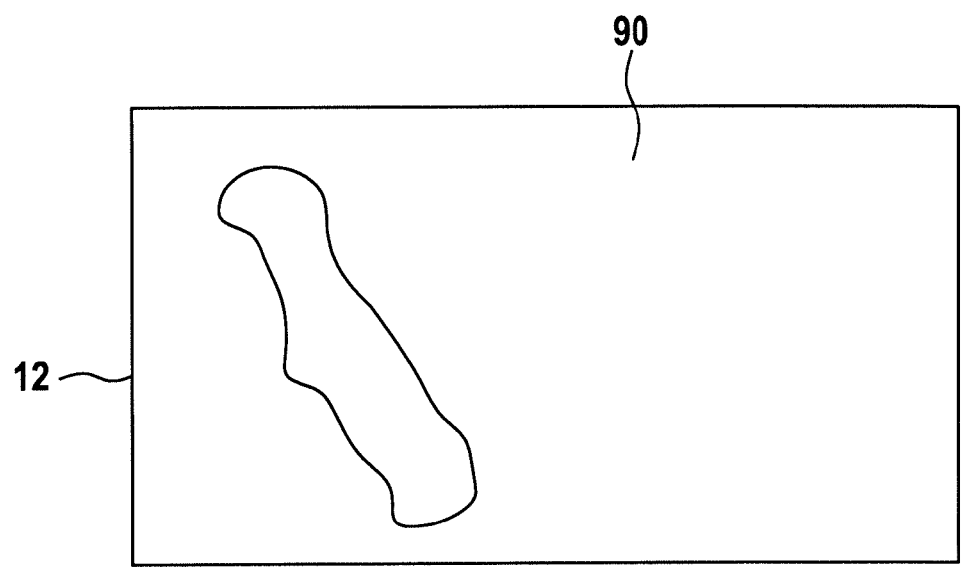

FIG. 6B illustrates an initial area of interest 90 of the first digital microscopic tissue image 30. In the depicted exemplary embodiment, the initial area of interest 90 of the first digital microscopic tissue image 30 is a full view of the first digital microscopic tissue image 30. It is also possible that a portion of the first digital microscopic tissue image 30 is displayed as the initial area of interest of the first digital microscopic tissue image 30. For example, in case the user previously looked at the first digital microscopic tissue image 30 in the analysis of the patient-specific image record, the last area of interest of the previous inspection of the first digital microscopic tissue image 30 may be displayed as the initial area of interest for the current inspection of the first digital microscopic tissue image 30. The initial area of interest 90 is then displayed on the primary screen 12, as illustrated in FIG. 6B.

FIG. 7 illustrates exemplary steps of a method of determining and displaying an area of interest of a digital microscopic tissue image in accordance with an exemplary embodiment of the invention. In particular, FIG. 7 illustrates an example of switching from a particular one of the plurality of digital microscopic tissue images to a different one of the plurality of digital microscopic tissue images. The method steps, illustrated in FIG. 7, may start from any area of interest of the second digital microscopic tissue image 32, such as from the display of any of the areas of interest 80, 82, 84, 86 on the primary screen 12, as depicted in FIGS. 2C, 3B, 4B, and 5B.

Figure 7A:
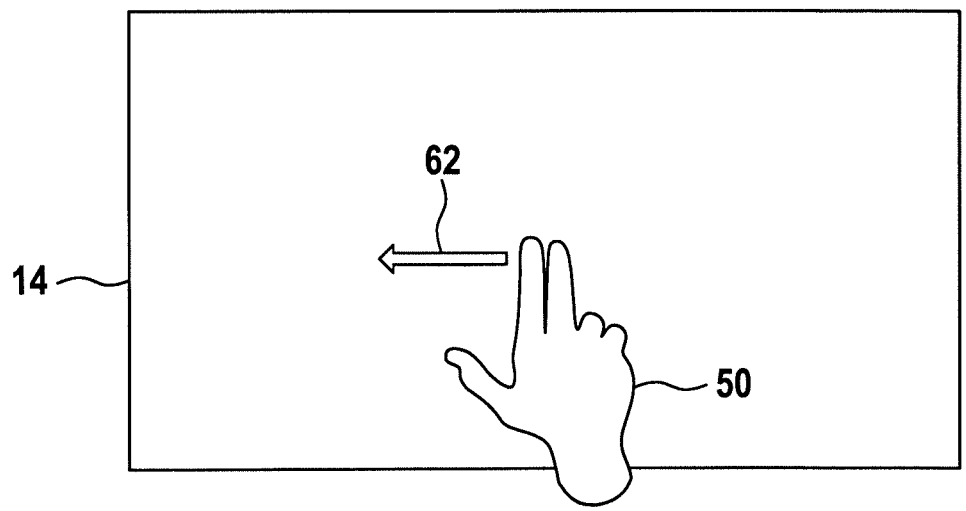

FIG. 7A illustrates that the touch screen 14 receives a sideways two-finger pan gesture 62 towards the left from a user. This is illustrated in FIG. 7A by the index finger and the middle finger of the hand 50 performing a lateral motion on the touch screen 14 towards the left. The two-finger pan gesture 62 is indicated with an arrow pointing towards the left from the index and middle fingers of the hand 50.

The two-finger pan gesture 62 is part of the second class of touch gestures, which are commands for switching from a particular one of the plurality of digital microscopic tissue images to a different one of the plurality of the digital microscopic tissue images. The two-finger pan touch gesture 62 towards the left is in particular interpreted as a command to switch to a next one of the plurality of digital microscopic tissue images. In the case of FIG. 7, the two-finger pan touch gesture 62 towards the left is interpreted as a command to switch to the third digital microscopic tissue image 34.

Figure 7B:
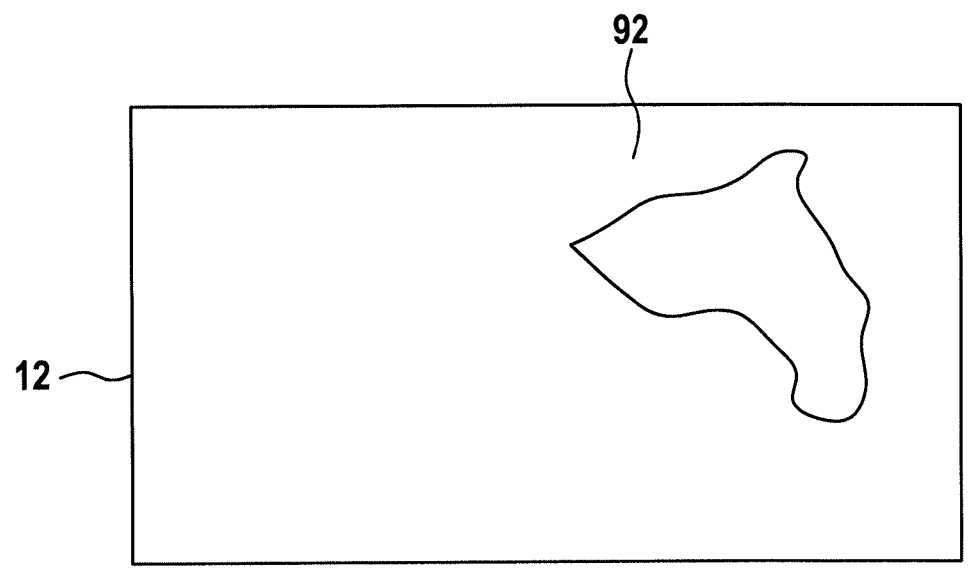

FIG. 7B illustrates an initial area of interest 92 of the third digital microscopic tissue image 34. In the depicted exemplary embodiment, the initial area of interest 92 of the third digital microscopic tissue image 34 is a full view of the third digital microscopic tissue image 34. It is also possible that a portion of the third digital microscopic tissue image 34 is displayed as the initial area of interest of the third digital microscopic tissue image 34. For example, in case the user previously looked at the third digital microscopic tissue image 34 in the analysis of the patient-specific image record, the last area of interest of the previous inspection of the third digital microscopic tissue image 34 may be displayed as the initial area of interest for the current inspection of the third digital microscopic tissue image 34. The initial area of interest 92 is then displayed on the primary screen 12, as illustrated in FIG. 7B.

It is understood that the meaning of the two-finger pan to the right and the two-finger pan to the left may be reversed, i.e. that the two-finger pan to the right is interpreted as a command to switch to a next one of the plurality of digital microscopic tissue images and that the two-finger pan to the left is interpreted as a command to switch to a previous one of the plurality of digital microscopic tissue images. The convention may be set in accordance with the particulars of the input/output system in question, in accordance with user preferences, etc.

The second class of touch gestures may also comprise two-finger pan gestures towards the top and/or towards the bottom and/or other multi-finger pan gestures and/or other touch gestures suitable for intuitively communicating an image switching command.

Some or all of the exemplary method steps, illustrated with respect to FIGS. 2-7, may be combined in a method of determining and displaying an area of interest of a digital microscopic tissue image in accordance with an exemplary embodiment of the invention. The particular method steps carried out in a particular run/iteration of the method may depend on the particular touch gestures received at the touch-based input device. The method may behave differently depending on which particular touch gestures out of the first and second classes of touch gestures are received.

While the touch gestures of FIGS. 2-7 are depicted to be performed with the right hand, it is understood that they may also be performed with the left hand, e.g. in the set-up of the work place of FIG. 1. The hand to be used may depend on the positions of the touch screen 14 and the user.

For clarity of illustration, the touch screen 14 is depicted in FIGS. 3-7 as a substantially empty screen, accepting touch gestures from the user. It is understood that the touch screen 14 may also display an image and accept touch gestures from the user. For example, the touch screen 14 may mirror the image output of the primary screen 12 and accept touch gestures on this mirrored image output. Further, the method may allow for the user to switch between the mode of accepting touch gestures, as illustrated in FIGS. 3-7, and the preview mode for selecting a particular one of the plurality of digital microscopic tissue images, as illustrated in FIGS. 2A and 2B, at any point in the analysis of the patient-specific image record.

Figure 8:
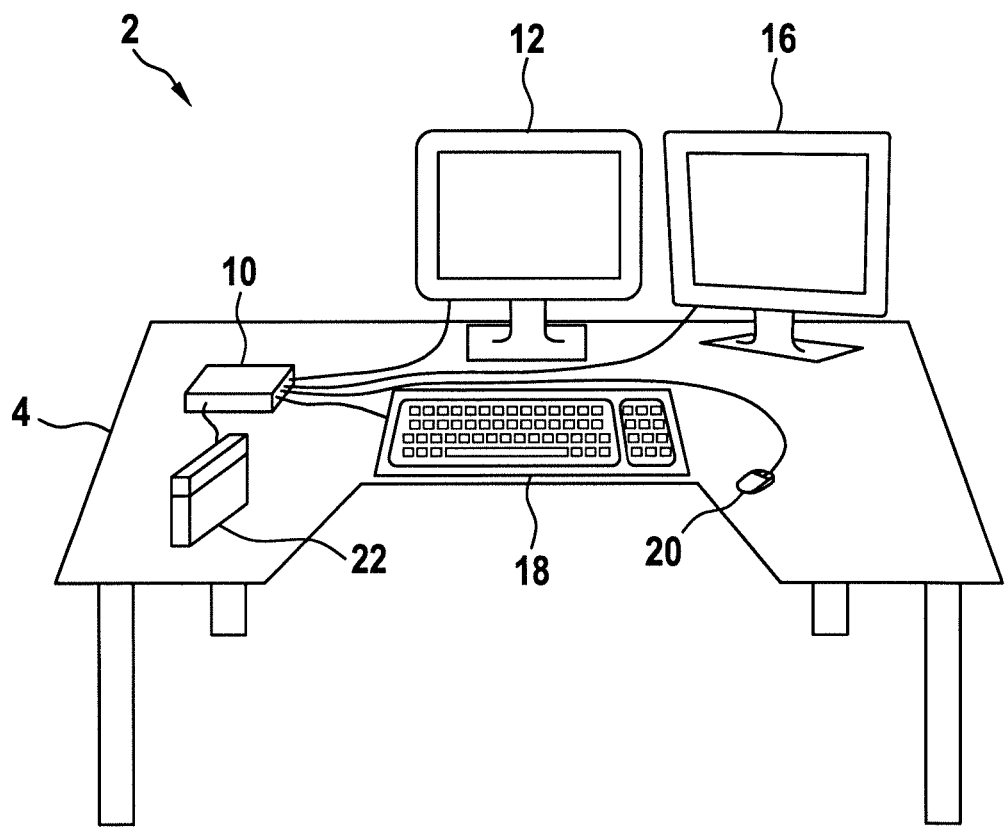
FIG. 8 shows a work place in accordance with another exemplary embodiment of the invention in a perspective view, the work place being equipped with an input/output system in accordance with another exemplary embodiment of the invention and the work place providing an environment for a method of determining and displaying an area of interest of a digital microscopic tissue image in accordance with another exemplary embodiment of the invention.

FIG. 8 shows a work place 2 in accordance with another exemplary embodiment of the invention in a perspective view. The work place 2 of FIG. 8 is similar to the work place 2 of FIG. 1. Like elements are denoted with the same reference numerals, and reference is made to the description thereof above. The work place 2 of FIG. 8 differs from the work place 2 of FIG. 1 in that the touch screen 14 is replaced with a motion sensor 22. The motion sensor 22 is configured to detect touchless motion gestures from a user. The word touchless indicates that no physical contact between the motion sensor 22 and the user, in particular between the motion sensor 22 and the user's hand, is necessary for conveying input data to the motion sensor 22.

In the exemplary embodiment of FIG. 8, the motion sensor 22 comprises an upper motion sensor bar and a lower portion, which is a stand-like structure for the upper motion sensor bar and which may house circuitry for processing signals from the upper motion sensor bar. The motion sensor 22 has an overall cuboid outer shape and is positioned upright on the desk 4. The motion sensor may have any other shape and set-up that is suitable for detecting touchless motion gestures from a user.

The motion sensor 22 is directed towards a region at or above a tabletop of the desk 4. In particular, the motion sensor may be directed to a region at the tabletop of the desk 4 similar to the position of the touch screen 14 in the exemplary embodiment of FIG. 1. In this way, the user may conveniently and ergonomically perform touchless motion gestures that are detected by the motion sensor 22. The touchless motion gestures are an alternative way of inputting commands for navigating through the patient-specific image record.

The touchless motion gestures may correspond to the touch gestures, discussed above with respect to the touch screen 14. It is also possible that additional and/or alternative gestures are accepted by the motion sensor 22. Again, the motion sensor accepts a first class of touchless motion gestures, which result in an updated area of interest of the particular one of the plurality of digital microscopic tissue images being determined and displayed, and a second class of touchless motion gestures, which result in a switching from the particular one of the plurality of digital microscopic tissue images to a different one of the plurality of digital microscopic tissue images and an initial area of interest of the different one of the plurality of digital microscopic tissue images being displayed.

Figure 9:
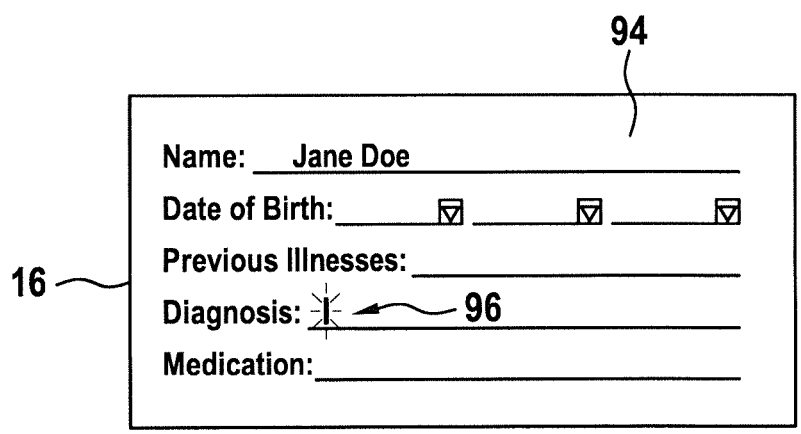
FIG. 9 shows an exemplary patient-specific text-based record, as employed in a method of determining and displaying an area of interest of a digital microscopic tissue image in accordance with an exemplary embodiment of the invention.

FIG. 9 shows an exemplary excerpt of a patient-specific text-based record 94, as may be displayed on the tertiary screen 16 in the work place 2 of FIG. 1 or FIG. 8. In the depicted exemplary excerpt of FIG. 9, the five input fields "Name", "Date of Birth", "Previous Illnesses", "Diagnosis", and "Medication" are shown. While the input field "Date of Birth" has three subfields for day, month, and year, which may be populated via drop down menus, the other four input fields are text fields.

FIG. 9 further shows a cursor 96, which indicates which input field currently has the input focus, i.e. to which input field a data input would be written. The cursor 96 may be a blinking cursor bar, as illustrated in FIG. 9, or a frame around a particular input field or a color highlighting of a particular input field or any other suitable marker for indicating the input field accepting data input.

In the exemplary work places 2 of FIGS. 1 and 8, the patient-specific text-based record 94 is depicted on the tertiary screen 16 and can be accessed/populated via the keyboard 18 and the mouse 20. Both the keyboard 18 and the mouse 20 may be used for issuing cursor placement commands, i.e. for moving the cursor 96 to a desired position. Further, both the keyboard 18 and the mouse 20 may be used for data input into the patient-specific text-based record 94. With the help of the mouse 20, the user may provide data input via the drop down menus. With the help of the keyboard 18, the user may provide data input into text fields, drop down menus, etc.

In the context of the work place 2 of FIGS. 1 and 8, the keyboard 18 and the mouse 20 are used for manipulating the patient-specific text-based record 94, and the touch screen 14/motion sensor 22 is used for manipulating the tissue image output on the primary screen 12, as discussed above. In exemplary embodiments of the invention, the accepting of touch gestures on the touch screen 14 and the ensuing modification of the tissue image output on the primary screen 12 does not interfere with the position of the cursor 96 in the patient-specific text-based record 94 and does not interfere with the readiness of the patient-specific text-based record 94 to accept data input from the keyboard 18 and the mouse 20.

During analysis of the patient-specific image record and documentation in the patient-specific text-based record, a user may input text into the patient-specific text-based record 94 via the keyboard 18. At some point during the inputting of text, the user may (re)evaluate one or more of the digital microscopic tissue images by navigating through them via the touch screen 14/motion sensor 22. After the reception of a touch gesture on the touch screen 14/reception of a touchless motion gesture by the motion sensor 22, the method/system in accordance with an exemplary embodiment of the invention may provide for an updated tissue image output on the primary screen 12 and may return the input focus to the tertiary screen right away, with the cursor 96 being at the same position as before the touch gesture on the touch screen 14/touchless motion gesture. In this way, the user may continue inputting data into the patient-specific text-based record 94 in a seamless manner. In particular, no time-consuming re-placement of the cursor 96 and no time-consuming re-activation of the window containing the patient-specific text-based patient record 94 has to take place.

FIG. 10 illustrates various method steps of a method of determining and displaying an area of interest of a digital microscopic tissue image in accordance with another exemplary embodiment of the invention. In the exemplary method steps discussed with respect to FIGS. 2, 3, 4, 5, 6, and 7, the method displays a single digital microscopic tissue image or a portion of a single digital microscopic tissue image on the primary screen 12. In contrast thereto, the method illustrated with respect to FIG. 10 allows for the display of multiple digital microscopic tissue images/the display of portions of multiple digital microscopic tissue images on the primary screen 12.

Figure 10A:
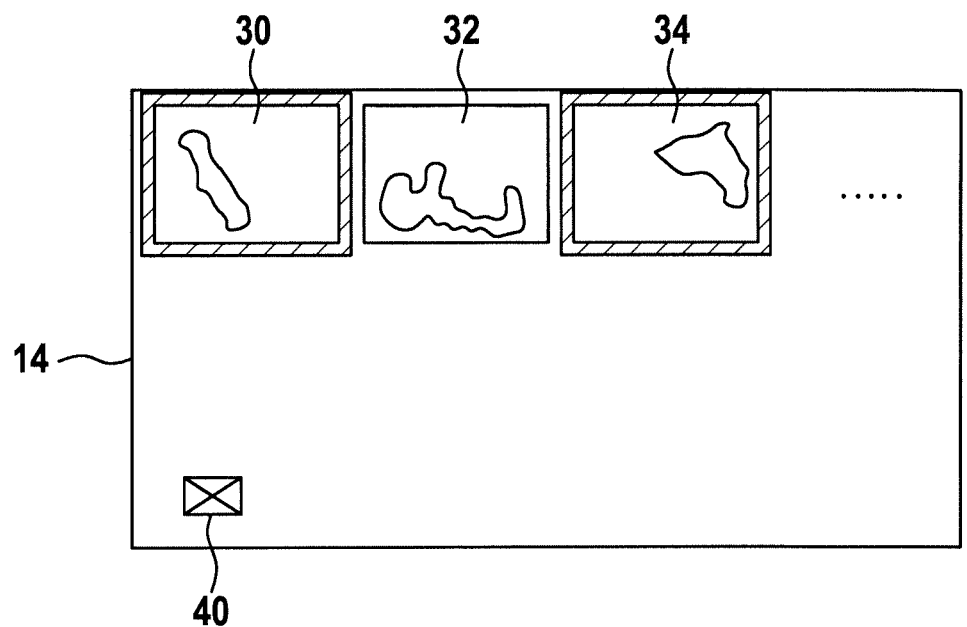
FIG. 10A-10D illustrate various method steps of a method of determining and displaying an area of interest of a digital microscopic tissue image in accordance with another exemplary embodiment of the invention.

FIG. 10A is similar to FIG. 2A. It also shows an exemplary situation at the beginning of the analysis of the patient-specific image record, when previews of some or all of the plurality of digital microscopic tissue images are displayed on the touch screen 14. Again, the first digital microscopic tissue image 30, the second digital microscopic tissue image 32, the third digital microscopic tissue image 34, and dots indicating potential further digital microscopic tissue images are depicted in FIG. 10A. In contrast to FIG. 2A, FIG. 10A shows a multi-select mode. This multi-select mode is indicated by the cross ticked in a box 40, displayed in the left bottom corner of the touch screen 14. By ticking said box 40, the user may enter or leave the multi-select mode. It is pointed out that the election of the multi-select mode may also be accepted in other ways, such as via a user input via the mouse 20 or the keyboard 18.

FIG. 10A depicts the exemplary situation that a user has selected both the first digital microscopic tissue image 30 and the third digital microscopic tissue image 34. This selection is indicated with respective frames around the previews of the first digital microscopic tissue image 30 and the third digital microscopic tissue image 34 on the touch screen 14. Instead of with frames, the selected digital microscopic tissue images may be indicated with other markers, such as arrows, color codes, check symbols, etc.

Upon receiving the selection of the first digital microscopic tissue image 30 and the third digital microscopic tissue image 34, the method displays a first initial area of interest 190 of the first digital microscopic tissue image 30 and a second initial area of interest 192 of the third digital microscopic tissue image 34 on the primary screen 12. In the exemplary embodiment of FIG. 10, the first initial area of interest 190 is a full view of the first digital microscopic tissue image 30 and the second initial area of interest 192 is a full view of the third digital microscopic tissue image 34. This is illustrated in FIG. 10B.

The method further assigns the input focus to one of the selected digital microscopic tissue images. In the exemplary embodiment of FIG. 10 and the exemplary situation of the first digital microscopic tissue image 30 and the third digital microscopic tissue image 34 being selected, the method assigns the input focus to the first initial area of interest 190. The input focus is indicated with a frame in FIG. 10B. The input focus may be indicated with other markers, such as an arrow, a color code, a check symbol, etc., allowing the user to know which of the displayed areas of interest has the input focus, i.e. which of the displayed areas of interest is the subject of commands given in the form of touch gestures. It is pointed out that the method may initially assign the input focus in an algorithmic manner or in a random manner.

Figure 10B:
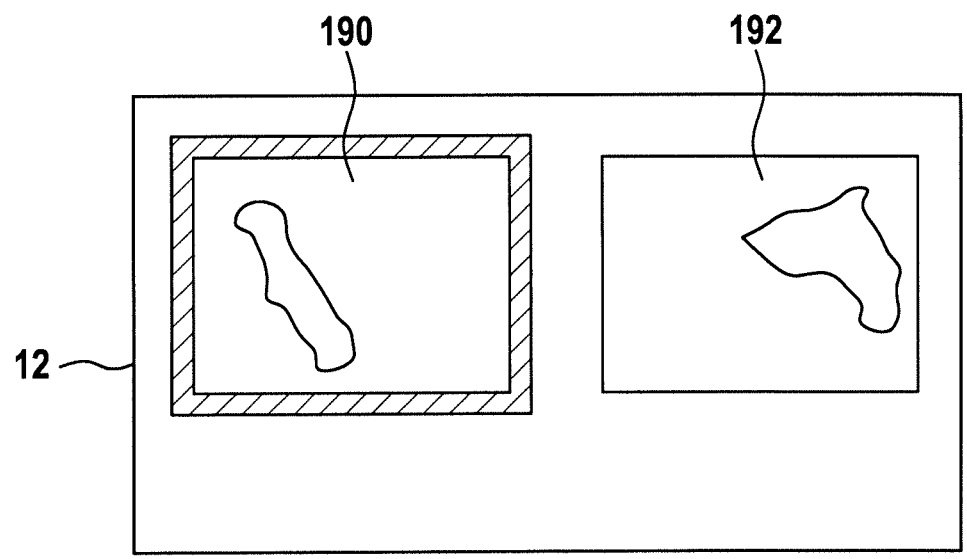

In the situation depicted in FIG. 10B, the first initial area of interest 190 has the input focus. Upon receiving a touch gesture from the first class of touch gestures, the method determines an updated area of interest of the first digital microscopic tissue image 30 and displays said updated area of interest of the first digital microscopic tissue image 30 on the primary screen 12 at the position and with the extension of the first initial area of interest 190. Reference is made to the description of exemplary updates of the area of interest with respect to FIGS. 3, 4, and 5. The touch gestures of the first class of touch gestures result in updated areas of interest being displayed on that portion of the primary screen 12 that has the input focus.

Figure 10C:
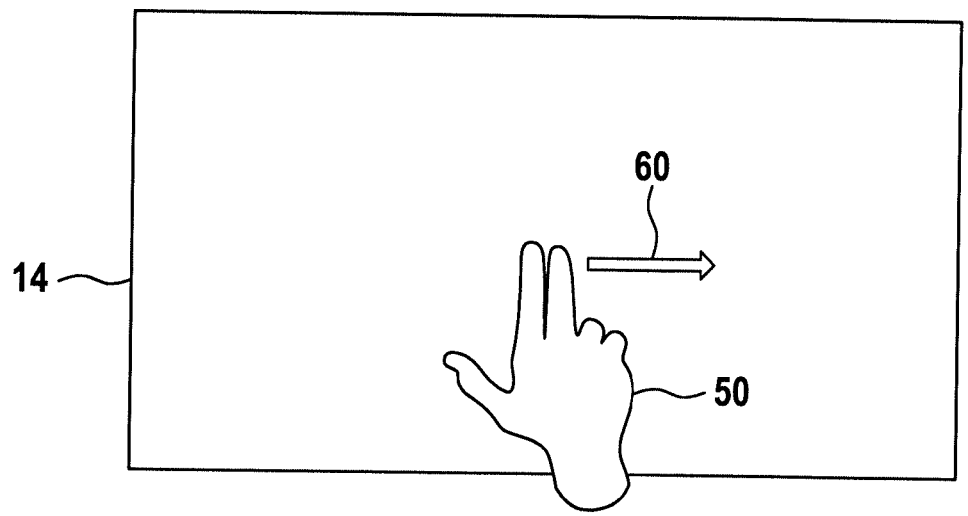
Figure 10D:
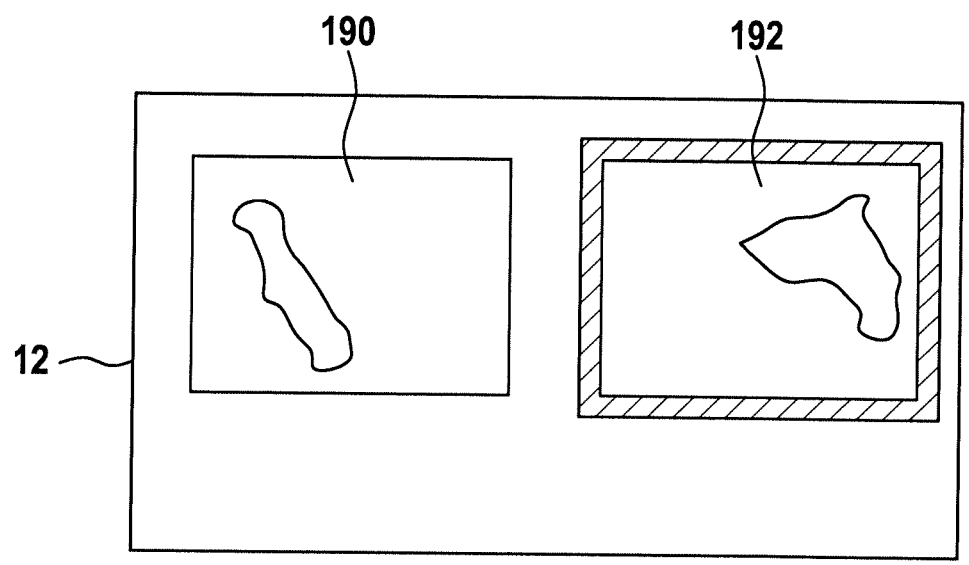

FIG. 10C illustrates the reception of a touch gesture from the second class of touch gestures. In particular, FIG. 10C illustrates the reception of a two-finger pan 60 towards the right. Upon receiving the two-finger pan 60 towards the right, the method switches the input focus from the first initial area of interest 190 to the second initial area of interest 192. This is illustrated in FIG. 10D, where the first initial area of interest 190 is no longer depicted with a frame, but where the second initial area of interest 192 is depicted with a frame. Upon subsequently receiving a touch gesture from the first class of touch gestures, the method determines an updated area of interest of the third digital microscopic tissue image 34 and displays said updated area of interest of the third digital microscopic tissue image 34 on the primary screen 12 at the position and with the extension of the second initial area of interest 192.

The method illustrated with respect to FIG. 10 allows for navigating through a particular one of the plurality of digital microscopic tissue images of the patient-specific image record via the first class of touch gestures and allows for switching the input focus between different digital microscopic tissue images, displayed simultaneously on the primary screen, via the second class of touch gestures. In this way, the patient-specific image record may be navigated in a quick and ergonomic manner, while allowing the user to view different ones of the plurality of digital microscopic tissue images concurrently.

The method illustrated with respect to FIG. 10 has been described in the context of the input/output system of FIG. 1. It is also applicable to the input/output system of FIG. 8. The first class of touchless motion gestures and the second class of touchless motion gestures may be used for updating the area of interest of that digital microscopic tissue image that has the input focus and for switching the input focus between displayed areas of interest of different digital microscopic tissue images, respectively. In the absence of the touch screen 14, the initial selection of multiple digital microscopic tissue images may be carried out in another suitable way, such as by displaying an arrangement of previews on the primary screen and selecting multiple digital microscopic tissue images via the mouse 20 or the keyboard 18.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed, but that the invention will include all embodiments falling within the scope of the appended claims.

The invention claimed is:

1. A method of determining and displaying an area of interest of a digital microscopic tissue image from a plurality of digital microscopic tissue images, the plurality of digital microscopic tissue images jointly forming a patient-specific image record, the method comprising:
    displaying an initial area of interest of a particular one of the plurality of digital microscopic tissue images on a primary screen, positioned in a forward viewing direction for a user sitting at a desk;
    accepting touch gestures from the user on a touch-based input device, such as a touch screen or a touch pad, the touch-based input device being positioned substantially horizontally at the desk;
    upon receiving a touch gesture from a first class of touch gestures, determining an updated area of interest within the particular one of the plurality of digital microscopic tissue images and displaying the updated area of interest of the particular one of the plurality of digital microscopic tissue images on the primary screen; and
    upon receiving a touch gesture from a second class of touch gestures, switching from the particular one of the plurality of digital microscopic tissue images to a different one of the plurality of digital microscopic tissue images and displaying an initial area of interest of said different one of the plurality of digital microscopic tissue images on the primary screen.

2. The method according to claim 1, wherein the first class of touch gestures comprises at least one of a one-finger pan, a two-finger pinch, a two-finger stretch, and a two-finger rotational motion and wherein the method comprises at least one of:
    in response to the one-finger pan, determining an updated area of interest that is laterally offset from the initial area of interest in the particular one of the plurality of digital microscopic tissue images;
    in response to the two-finger pinch, determining an updated area of interest whose relative size with respect to the particular one of the plurality of digital microscopic tissue images is increased, as compared to the initial area of interest of the particular one of the plurality of digital microscopic tissue images;
    in response to the two-finger stretch, determining an updated area of interest whose relative size with respect to the particular one of the plurality of digital microscopic tissue images is reduced, as compared to the initial area of interest of the particular one of the plurality of digital microscopic tissue images;
    in response to the two-finger rotational motion, determining an updated area of interest that is rotated with respect to the initial area of interest in the particular one of the plurality of digital microscopic tissue images.

3. The method according to claim 1, wherein the second class of touch gestures comprises at least one multi-finger pan, in particular at least one two-finger pan and/or at least one three-finger pan and/or at least one four-finger pan.

4. The method according to claim 1, wherein the second class of touch gestures comprises a sideways multi-finger pan towards the left and a sideways multi-finger pan towards the right, in particular a sideways two-finger pan towards the left and a sideways two-finger pan towards the right.

5. The method according to claim 1, wherein the method is carried out repeatedly.

6. The method according to claim 1, wherein the touch-based input device is a secondary screen and wherein the method further comprises:
displaying an arrangement of previews of at least a subset of the plurality of digital microscopic tissue images on the touch-based input device; and
upon receiving a touch-based image selection command from the user, the touch-based image selection command indicating a selected one of the plurality of digital microscopic tissue images, using the selected one of the plurality of digital microscopic tissue images as said particular one of the plurality of digital microscopic tissue images for the step of displaying an initial area of interest of a particular one of the plurality of digital microscopic tissue images on the primary screen.

7. The method according to claim 1, wherein the touch-based input device is a secondary screen and wherein the method comprises:
providing an image output on the secondary screen substantially corresponding to the area of interest displayed on the primary screen.

8. The method according to claim 1, wherein said displaying of an initial area of interest of said different one of the plurality of digital microscopic tissue images comprises displaying a full view of said different one of the plurality of digital microscopic tissue images or a previously displayed area of interest of said different one of the plurality of digital microscopic tissue images on the primary screen.

9. The method according to claim 1, further comprising:
displaying a patient-specific text-based record on a tertiary screen;
providing a cursor on the tertiary screen and accepting cursor placement commands and data input into the patient-specific text-based record from at least one additional input device, such as from a mouse and/or from a keyboard; and
when receiving touch gestures from the user on the touch-based input device, maintaining a position of the cursor on the tertiary screen and/or upholding a readiness of accepting data input into the patient-specific text-based record from the at least one additional input device.

10. A method of determining and displaying an area of interest of a digital microscopic tissue image from a plurality of digital microscopic tissue images, the plurality of digital microscopic tissue images jointly forming a patient-specific image record, the method comprising:
displaying an initial area of interest of a particular one of the plurality of digital microscopic tissue images on a primary screen, positioned in a forward viewing direction for a user sitting at a desk;
accepting touchless motion gestures from the user by a motion sensor, the motion sensor being directed towards a region at or above a tabletop of the desk;
upon receiving a touchless motion gesture from a first class of touchless motion gestures, determining an updated area of interest-within the particular one of the plurality of digital microscopic tissue images and displaying the updated area of interest of the particular one of the plurality of digital microscopic tissue images on the primary screen; and
upon receiving a touchless motion gesture from a second class of touchless motion gestures, switching from the particular one of the plurality of digital microscopic tissue images to a different one of the plurality of digital microscopic tissue images and displaying an initial area of interest of said different one of the plurality of digital microscopic tissue images on the primary screen.

11. An input/output system for navigating a patient-specific image record, comprising a plurality of digital microscopic tissue images, the system comprising:
a primary screen for displaying an area of interest of a digital microscopic tissue image, the primary screen being configured to be positioned substantially vertically; and
a touch-based input device for receiving touch gestures from a user, the touch-based input device being configured to be positioned substantially horizontally;
wherein the input/output system is configured to:
display an initial area of interest of a particular one of the plurality of digital microscopic tissue images on the primary screen;
determine an updated area of interest within the particular one of the plurality of digital microscopic tissue images upon receiving a touch gesture from a first class of touch gestures and display the updated area of interest of the particular one of the plurality of digital microscopic tissue images on the primary screen; and
switch from the particular one of the plurality of digital microscopic tissue images to a different one of the plurality of digital microscopic tissue images upon receiving a touch gesture from a second class of touch gestures and display an initial area of interest of said different one of the plurality of digital microscopic tissue images on the primary screen.

12. The input/output system according to claim 11, further comprising:
a tertiary screen for displaying a patient-specific text-based record, with a cursor being provided on the tertiary screen during operation; and
at least one additional input device, such as a mouse and/or a keyboard, for receiving cursor placement commands and data input into the patient-specific text-based record;
wherein the input/output system is configured, when receiving touch gestures from the user on the touch-based input device, to maintain a position of the cursor on the tertiary screen and/or to uphold a readiness of accepting data input into the patient-specific text-based record from the at least one additional input device.

13. A work place for a medical personnel user, such as a doctor or a pathologist or a medical assistant or a nurse, the work place comprising:
a desk; and
an input/output system according to claim 11;
wherein the primary screen is placed on the desk in a forward viewing direction of the user; and
wherein the touch-based input device is mounted to or integrated with the desk and is positioned substantially horizontally at the desk.

* * * * *